United States Patent
O'Sullivan et al.

(10) Patent No.: US 9,408,392 B2
(45) Date of Patent: Aug. 9, 2016

(54) COMPOUNDS

(71) Applicant: SYNGENTA PARTICIPATIONS AG, Basel (CH)

(72) Inventors: Anthony Cornelius O'Sullivan, Stein (CH); Olivier Loiseleur, Stein (CH); Daniel Stierli, Stein (CH); Torsten Luksch, Stein (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/375,801

(22) PCT Filed: Feb. 14, 2013

(86) PCT No.: PCT/EP2013/052949
§ 371 (c)(1),
(2) Date: Jul. 31, 2014

(87) PCT Pub. No.: WO2013/120940
PCT Pub. Date: Aug. 22, 2013

(65) Prior Publication Data
US 2014/0378461 A1 Dec. 25, 2014

(30) Foreign Application Priority Data
Feb. 14, 2012 (EP) .................... 12155413

(51) Int. Cl.
| | |
|---|---|
| *C07C 233/64* | (2006.01) |
| *C07C 233/65* | (2006.01) |
| *C07C 311/49* | (2006.01) |
| *C07D 213/81* | (2006.01) |
| *C07D 231/14* | (2006.01) |
| *C07D 233/64* | (2006.01) |
| *C07D 237/24* | (2006.01) |
| *C07D 239/28* | (2006.01) |
| *C07D 241/24* | (2006.01) |
| *C07D 307/68* | (2006.01) |
| *A01N 37/18* | (2006.01) |
| *A01N 43/40* | (2006.01) |
| *A01N 51/00* | (2006.01) |
| *A01N 43/08* | (2006.01) |
| *A01N 43/10* | (2006.01) |
| *A01N 43/12* | (2006.01) |
| *A01N 43/36* | (2006.01) |
| *A01N 43/42* | (2006.01) |
| *A01N 43/50* | (2006.01) |
| *A01N 43/54* | (2006.01) |
| *A01N 43/56* | (2006.01) |
| *A01N 43/80* | (2006.01) |
| *A01N 43/58* | (2006.01) |
| *A01N 43/60* | (2006.01) |

(52) U.S. Cl.
CPC ............... *A01N 51/00* (2013.01); *A01N 37/18* (2013.01); *A01N 43/08* (2013.01); *A01N 43/10* (2013.01); *A01N 43/12* (2013.01); *A01N 43/36* (2013.01); *A01N 43/40* (2013.01); *A01N 43/42* (2013.01); *A01N 43/50* (2013.01); *A01N 43/54* (2013.01); *A01N 43/56* (2013.01); *A01N 43/58* (2013.01); *A01N 43/60* (2013.01); *A01N 43/80* (2013.01); *C07C 233/64* (2013.01); *C07C 233/65* (2013.01); *C07C 311/49* (2013.01); *C07D 213/81* (2013.01); *C07D 231/14* (2013.01); *C07D 233/64* (2013.01); *C07D 237/24* (2013.01); *C07D 239/28* (2013.01); *C07D 241/24* (2013.01); *C07D 307/68* (2013.01)

(58) Field of Classification Search
None
See application file for complete search history.

(56) References Cited

U.S. PATENT DOCUMENTS

2009/0093525 A1    4/2009   Bois et al.

FOREIGN PATENT DOCUMENTS

| | | |
|---|---|---|
| EP | 1997800 A1 | 12/2008 |
| WO | 2006/122952 A1 | 11/2006 |
| WO | 2006/122955 A1 | 11/2006 |
| WO | 2007/134799 A1 | 11/2007 |
| WO | 2009/052078 A1 | 4/2009 |

OTHER PUBLICATIONS

Tanaka, et al., J. Med. Chem., 54:851 (Dec. 30, 2010).*
International Search Report from International Application No. PCT/EP2013/052949, Oct. 15, 2013.

* cited by examiner

*Primary Examiner* — Michael Barker
(74) *Attorney, Agent, or Firm* — Brian D. McAlhaney

(57) ABSTRACT

Compounds of the formula (I), in which the substituents are as defined in claim 1, are suitable for use as nematicides.

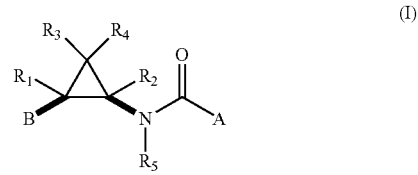

15 Claims, No Drawings

COMPOUNDS

This application is a 371 filing of International Application No. PCT/EP2013/052949, filed Feb. 14, 2013, which claims priority benefit to European Patent No. 12155413.3 filed Feb. 14, 2012, the contents of all of which are incorporated herein by reference.

The present invention relates to novel nematicidal compositions, novel compounds, the process for the preparation of these compounds and their use as nematicides.

Compounds with nematicidal activity are described, for example, in WO 2007/108483, WO0160783 and WO03027059.

It has now been found that certain cyclopropylcarboxamides characterized by a cis substituted cyclopropyl ring have good nematicidal activity.

The present invention thus relates to a nematicidal composition, which, in addition to comprising formulation adjuvants, comprises a nematicidal effective amount of a compound of formula I

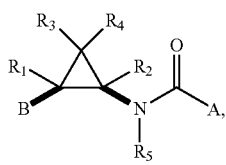

wherein
A is a 5- or 6-membered heteroaryl containing 1 to 3 heteroatoms, each independently selected from oxygen, nitrogen and sulphur, or phenyl, wherein the heterocyclic or the phenyl ring are unsubstituted or substituted by $R_6$, where
$R_6$ is, independently of each other, halogen, cyano, C1-C4-alkyl, C1-C4-haloalkyl, C1-C4-alkoxy, C1-C4-haloalkoxy, C1-C4-haloalkylthio, C1-C4-alkoxy-C1-C4-alkyl or C1-C4-haloalkoxy-C1-C4-alkyl,
$R_1, R_2, R_3$ and $R_4$, independently of each other, are hydrogen, halogen, cyano, C1-C4-alkyl or C1-C4-haloalkyl,
$R_5$ is hydrogen or hydroxyl,
B is a mono- or bicyclic 5 to 10 membered heteroaromatic ring system containing 1 to 5 heteroatoms, each independently selected from oxygen, nitrogen and sulphur, or a mono- or bicyclic 5 to 10 membered aromatic ring, wherein the heteroaromatic ring or the aromatic ring is unsubstituted or substituted by R9, where
R9 is, independently of each other, halogen, cyano, R8, —OR8, —C(O)R8, —OC(O)R8, —NR7R8, —NR7C(O)R8, —NR7S(O)nR8, —S(O)nR8, —S(O)nNR7R8, —C(O)OR8 or C(O)NR7R8, where n is 0, 1, or 2,
R7 is, independently of each other, hydrogen, C1-C4-alkyl, C1-C4-haloalkyl, benzyl or phenyl, where benzyl or phenyl is unsubstituted or substituted with halogen, cyano, C1-C4-alkyl or C1-C4-haloalkyl, and
R8 is, independently of each other, C1-C4-alkyl, which is unsubstituted or substituted by R10, C3-C6-cycloalkyl, which is unsubstituted or substituted by R10, C6-C14-bicycloalkyl, which is unsubstituted or substituted by R10, C2-C4-alkenyl, which is unsubstituted or substituted by R10, C2-C4-alkynyl, which is unsubstituted or substituted by R10, phenyl, which is unsubstituted or substituted by R10, or heteroaryl, which is unsubstituted or substituted by R10, where R10 is, independently of each other, hydroxyl, halogen, cyano, C1-C4-alkyl, C1-C4haloalkyl, C1-C4-alkoxy, C1-C4-haloalkoxy, C1-C4-alkylthio, C1-C4-haloalkylthio, C2-C4-alkenyloxy, C2-C4-alkynyloxy, formyl, C1-04-alkylcarbonyl, C1-C4alkoxycarbonyl or halophenyl,
wherein B and A-CO—NR5 are cis to each other on the cyclopropyl ring, and tautomers, isomers, enantiomers of these compounds.

The compounds of formula (I) and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case. This invention accordingly covers all such isomers and tautomers and mixtures thereof in all proportions as well as isotopic forms such as deuterated compounds. As an example, the compounds of the invention may contain one or more asymmetric carbon atoms, for example, at the —$CR^2N$—, —$CR^1B$—, and —$CR^3R^4$— groups, and the compounds of formula (I) may exist as enantiomers (or as pairs of diastereoisomers) or as mixtures of such.

The invention also covers salts and N-oxides of each compound for formula (I).

One skilled in the art also recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts amongst agriculturally and/or physiologically tolerable salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Suitable amongst agriculturally and/or physiologically tolerable salts can also be the salts of those cations which do not adversely affect the pesticidal and/or parasiticidal action of the compounds of formula (I). Thus, especially suitable cations are the ions of the alkali metals including sodium, potassium and lithium, of the alkaline earth metals including calcium and magnesium, and of the transition metals including manganese, copper, iron, zinc, cobalt, lead, silver, nickel, and also ammonium or organic ammonium including monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, C5-C6-cycloalkylammonium, piperidinium, morpholinium, pyrrolidinium, or benzylammonium, moreover phosphonium ions, sulfonium ions, preferably tri(C1-C4-alkyl) sulfonium and sulfoxonium ions, preferably tri (C1-C4-alkyl) sulfoxonium.

Alkyl groups (either alone or as part of a larger group, such as alkoxy-, alkylsulfanyl-, alkylsulfinyl-, alkylsulfonyl-, alkylcarbonyl- or alkoxycarbonyl-) can be in the form of a straight or branched chain and are, for example, methyl, ethyl, 1-propyl, prop-2-yl, 1-butyl, but-2-yl, or 2-methyl-prop-2-yl. The alkyl group (either alone or as part of a larger group, such as alkoxy-, alkylsulfanyl-, alkylsulfinyl-, alkylsulfonyl-, alkylcarbonyl- or alkoxycarbonyl-), in each embodiment of the invention, is preferably C1-C3-alkyl, more preferably C1-C2-alkyl, especially methyl group. In the instance of alkoxy, examples are methoxy, ethoxy, propoxy, n-butoxy, isobutoxy and also their isomeric groups; preferably, independent of other embodiments, methoxy and ethoxy, especially methoxy.

Alkenyl groups can be in the form of straight or branched chains, and can be, where appropriate, of either the (E)- or (Z)-configuration. Examples are vinyl and allyl. The alkenyl group, in each embodiment of the invention, is preferably a C2-C3-alkenyl group, more preferably vinyl or allyl group.

Alkynyl groups can be in the form of straight or branched chains. Examples are ethynyl and propargyl. The alkynyl group, in each embodiment of the invention, is preferably a C2-C3-alkynyl group, more preferably propargyl group.

Halogen is fluorine, chlorine, bromine or iodine; halogen, in each embodiment of the invention, is fluorine, chlorine, or bromine; especially fluorine or chlorine.

Haloalkyl groups (either alone or as part of a larger group, such as haloalkoxy-, haloalkylsulfanyl-, haloalkylsulfinyl- or haloalkylsulfonyl-) are alkyl groups which are substituted by one or more of the same or different halogen atoms and are, for example, fluoromethyl, difluoromethyl, trifluoromethyl, chlorodifluoromethyl and 2,2,2-trifluoro-ethyl. The haloalkyl group (either alone or as part of a larger group, such as haloalkoxy-, haloalkylsulfanyl-, haloalkylsulfinyl- or haloalkylsulfonyl-), in each embodiment of the invention, is preferably trifluoromethyl. In instance of haloalkoxy, examples are fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2,2,2-trifluoroethoxy, 2-chloroethoxy and trifluoromethoxy Cycloalkyl groups are mono-cyclic and are, for example, cyclopropyl, cyclobutyl, cyclopentyl and cyclohexyl. The C3-C6-cycloalkyl group, in each embodiment of the invention, is preferably a C3-C5-cycloakyl, more preferably a C3-C4-cycloalkyl group, especially a C3-cycloalkyl group. Where a cycloalkyl moiety is said to be substituted, the cycloalkyl moiety is preferably substituted by one to four substituents, more preferably by one to three substituents, such as one or two substituents, especially by one substitutent. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl and tert-butoxycarbonyl; preferred are methoxycarbonyl, ethoxycarbonyl and isopropoxycarbonyl.

Alkylsulfanyl group is, for example, methylsulfanyl, ethylsulfanyl, propylsulfanyl, isopropylsulfanyl, n-butylsulfanyl, isobutylsulfanyl, sec-butylsulfanyl and tert-butylsulfanyl Examples of haloalkylsulfanyl are chloro- and/or fluoro-halogenated substituents thereof, such as difluoromethylsulfanyl, trifluoromethylsulfanyl, chlorodifluoromethylsulfanyl and 2,2,2-trifluoro-ethylsulfanyl.

Alkylsulfinyl is, for example, methylsulfinyl, ethylsulfinyl, propylsulfinyl, isopropylsulfinyl, n-butylsulfinyl, isobutylsulfinyl, sec-butylsulfinyl, and tert-butylsulfinyl. Examples of haloalkylsulfinyl are chloro- and/or fluoro-halogenated substituents thereof, such as difluoromethylsulfinyl, trifluoromethylsulfinyl, chlorodifluoromethylsulfinyl and 2,2,2-trifluoro-ethylsufhinyl.

Alkylsulfonyl group is, for example, methylsulfonyl, ethylsulfonyl, propylsulfonyl, isopropylsulfonyl, n-butylsulfonyl, isobutylsulfonyl, sec-butylsulfonyl and tert-butylsulfonyl. Examples of haloalkylsulfonyl are chloro- and/or fluoro-halogenated substituents thereof, such as difluoromethylsulfonyl, trifluoromethylsulfonyl, chlorodifluoromethylsulfonyl and 2,2,2-trifluoro-ethylsulfonyl.

Alkoxyalkyl is, for example, methoxymethyl, 2-methoxyethyl, ethoxymethyl, 2-ethoxyethyl, n-propoxymethyl, n-propoxy-2-ethyl, isopropoxymethyl and 1-isopropoxyethyl. The alkoxyalkyl group, in each embodiment of the invention, is preferably a C1-C4-alkoxy-C1-C4-alkyl, more preferably a C1-C2-alkoxy-methyl, such as methoxymethyl and ethoxymethyl groups.

Aryl groups (either alone or as part of a larger group, such as aryl-alkylene-) are aromatic ring systems which can be mono-, bi- or tricyclic. Examples of such rings include phenyl, naphthyl, anthracenyl, indenyl or phenanthrenyl. Preferred aryl groups are phenyl and naphthyl, phenyl being most preferred.

Examples of cycloalkylcarbonyl are cyclopropylcarbonyl, cyclobutylcarbonyl, cyclopentylcarbonyl and cyclohexylcarbonyl; preferred are cyclopropylcarbonyl and cyclobutylcarbonyl.

Examples of cycloalkoxycarbonyl are cyclopropyloxycarbonyl, cyclobutyloxycarbonyl, cyclopentyloxycarbonyl and cyclohexyloxycarbonyl; preferred are cyclopropyloxycarbonyl and cyclobutyloxycarbonyl.

The term "heteroaryl" refers to aromatic ring systems containing at least one heteroatom and consisting either of a single ring or of two fused rings. Preferably, single rings will contain up to 3 and bicyclic systems up to 5, heteroatoms, which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

Compounds of formula I can occur in at least two enantiomeric forms: 1aa and 1ab. Substituents B and A-CO—NR5 are cis to each other in each of these enantiomers 1aa and 1ab. The difference between 1aa and 1ab is that the two carbon atoms bearing the B and the A-CO—NR5 groups each have their absolute stereochemistry formally inverted.

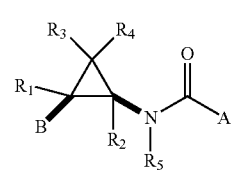

relative stereochemistry (I)

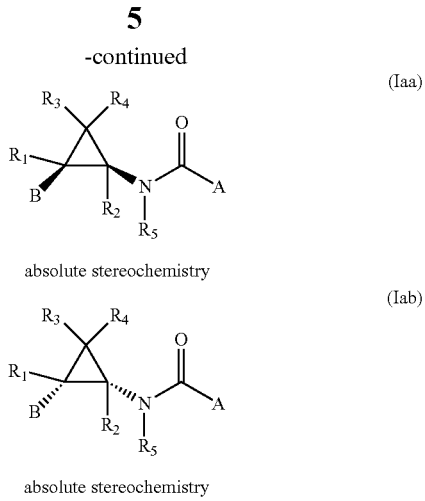

absolute stereochemistry absolute stereochemistry

A racemic compound formula (I) contains Iaa and Iab in a 50:50 ratio. Other ratios of Iaa and Iab are possible and part of the present invention. Examples of such ratios of Iaa to Iab are 1:99, 2:98, 5:95, 10:90, 20:80, 30:70; 40:60, 45:55; 55:45; 60:40, 70:30, 80:20, 90:10, 95:5, 98; 2, and 99:1. In a preferred embodiment, the weight ratio of Iaa to Iab is weighted towards compound of formula Iab, for example, the ratio of 1aa to Iab being 1:99, 2:98, 5:95, 10:90, 20:80, 30:70; 40:60, or 45:55. This ratio likewise applies to each and every formula I, such as such as any one of compounds of formulae (I), (Ia), (Ib), (Ic), (Id), (Ie), and each relevant intermediate described herein therefor.

The trans isomers of compounds of formula I, wherein B and A-CO—NR5 are trans to each other on the three-membered ring, can be formed as side products in the synthesis of compounds of the formula I. Mixtures containing up to 50, preferably up to 40, more preferably up to 30, especially up to 20, advantageously up to 10, desirably up to 5, in particular up to 3, % by weight, of the trans isomer are understood to be also part of this invention, such as any one of compounds of formulae (I), (Ia), (Ib), (Ic), (Id), (Ie), and each relevant intermediate described herein therefor.

It is possible that compounds of the formula I have further stereochemical centres, either at the carbon bearing R3 and R4, or in one of the substituents. Further isomers are then possible. The invention covers all those isomers and mixtures thereof in any ratio.

The compounds of the formula I may occur in different tautomeric forms. The invention Preferably, A is an optionally substituted 5- or 6-membered heteroaromatic ring, which contains, preferably, an oxygen atom or one or two nitrogen atoms, such as furyl, pyridyl, pyrimidinyl, pyrazinyl, and pyridazinyl, in particular pyridyl, or A is preferably an optionally substituted phenyl. In an embodiment of A, there are 1 to 3, preferably 1 or 2, substitutents R6 on A.

More preferably A is a optionally substituted 6-membered heteroaromatic ring, which contains 1 or 2 nitrogen atoms (e.g. pyridyl, pyrimidinyl, pyrazinyl, and pyridazinyl, in particular pyridyl) or A is preferably an optionally substituted phenyl.

Preferred substituents (R6), independently of each other, and independently of the ring type, is selected from C1-C4-alkyl, C1-C4-haloalkyl (in particular di- and trifluoromethyl), C1-C4-haloalkoxy, cyano and halogen, in particular trifluoromethyl, fluoro and chloro.

Most preferably, A, independent of other embodiments, is pyridyl, pyrimidinyl, pyrazinyl, or phenyl, which can be unsubstituted or substituted by one or two substituents R6, which can be independently selected from chloro, fluoro, trifluoromethyl, methyl, bromo, and cyano.

The preferable point or points of attachment of these substituents is ortho to the point of attachment of A to C(O)NR5.

Preferred examples of A, independent of other embodiments, are 2,6-difluorophenyl (A1); 2-chloro-3-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); 3-methyl-2-pyridyl (A11); 2-methyl-3-pyridyl (A22); 3-methyl-2-pyrazinyl (A24); 3-bromo-2-pyrazinyl (A25); 3-trifluoromethyl-2-pyrazinyl (A26); and 2-cyanophenyl (A29).

Particularly preferred A, independent of other embodiments, is selected from 2-chloro-3-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); 3-methyl-2-pyrazinyl (A24); 3-bromo-2-pyrazinyl (A25); and 3-trifluoromethyl-2-pyrazinyl (A26).

Especially preferred A, independent of other embodiments, is selected from 2-chloro-3-pyrazinyl (A2); 3-trifluoromethyl-2-pyridyl (A3); 2-trifluoromethyl-3-pyridyl (A5); 2-trifluoromethyl-phenyl (A6); 2-chloro-3-pyridyl (A7); and 3-trifluoromethyl-2-pyrazinyl (A26); advantageously 2-chloro-3-pyrazinyl (A2); 2-trifluoromethyl-3-pyridyl (A5); 2-trifluoromethyl-phenyl (A6); and 3-trifluoromethyl-2-pyrazinyl (A26).

Preferably, R1, R2, R3 and R4 are, independently of each other, hydrogen, halogen, C1-C4-alkyl or C1-C4-haloalkyl. In an embodiment, independent of other embodiments, R1, R2, R3 and R4 are each hydrogen.

Preferably R5, in any embodiment of formula I, is hydrogen.

B is preferably a 5 to 10 membered mono- or bi-cyclic ring system, which may contain 1 or 2 heteroatoms, independently selected, from nitrogen, oxygen and sulphur, which ring system is substituted by substituents (R9). In an instance, there are 1 to 3 substitutents R9 on B. Preferably substituent R9, independently from each other, is selected from halogen, cyano, C1-C4-alkyl, C1-C4-haloalkyl, C1-C4-haloalkoxy, C3-C6-cyclopropyl, C1-C4-haloalkyl-C3-C6-cycloalkyl, C1-C4-alkylthio, C1-C4-haloalkylthio, C1-C4-alkylsulfonyl, C1-C4-haloalkylsulfonyl, C1-C4-alkylsulfoxide, C1-C4-haloalkylsulfoxide, benzyloxy, a heteroaryl selected from pyridyl, pyridyloxy, pyrimidinyl, pyridazinyl, pyrazinyl, imidazolyl, pyrazolyl, pyrrolyl, thienyl, benzylthiophenyl, oxazolyl, quinolinyl, isoquinolinyl, furyl or benzofuryl, each of which can be unsubstituted or can have 1 to 3 substituents, independently selected, from halogen, cyano, hydroxyl, C1-C4-alkyl, C1-C4-haloalkyl, C1-C4-alkoxy, C1-C4-alkylthio, formyl, acetyl, and C1-C4-alkoxycarbonyl.

In an embodiment, independent of other embodiments, B is a phenyl substituted with 1 to 3 substiutents, independently, selected from halogen, cyano, C1-C4-alkyl, C1-C4-haloalkyl, C1-C4-haloalkoxy, C3-C6-cycloalkyl and C1-C4-haloalkyl-C3-C6-cycloalkyl. In a preferred embodiment, the substitutents are independently selected from bromo, chloro, fluoro, trifluoromethyl, difluoromethoxy, trifluoromethoxy and cyclopropyl.

In a group of preferred compounds of the formula I, B is a phenyl, which is unsubstituted or substituted by halogen, cyano, C1-C4-haloalkyl, C1-C4-haloalkoxy, cyclopropyl, imidazolyl, pyrazolyl, C1-C4-alkylthio, C1-C4-alkylsulfoxide, C1-C4-alkylsulfonyl, C1-C4-haloalkylthio, C1-C4-haloalkylsulfoxide or C1-C4-haloalkylsulfonyl, A is phenyl, pyrazolyl, pyridyl, pyrimidinyl, pyridazinyl, pyrazinyl or furyl, where these rings are substituted by C1-C4-alkyl, C1-C4-alkoxy, C1-C4-haloalkoxy, C1-C4-haloalkyl or halogen, and R1, R2, R3, R4 and R5 are hydrogen. More preferably, in this group of compounds, B is a phenyl substituted by halogen, cyano, C1-C4-haloalkyl or C1-C4-haloalkoxy. Most preferably, in this group of compounds, A is a phenyl, substituted by C1-C4-alkyl, C1-C4-alkoxy, C1-C4-haloalkoxy, C1-C4-haloalkyl or halogen.

In another group of preferred compounds of the formula I, B is phenyl or pyridyl, which can be unsubstituted or substituted by halogen or haloalkoxy, A is phenyl or pyridyl, which is substituted by C1-C4-alkyl or C1-C4-haloalkyl, R1 is hydrogen, C1-C4-alkyl or halogen, R3 is hydrogen or C1-C4-alkyl, and R2, R4 and R5 are each hydrogen.

In another group of preferred compounds of the formula I, B is a phenyl substituted by furyl, thienyl, pyrazolyl, pyridyl, pyrimidinyl, pyrrolyl, imidazolyl, oxazolyl, benzothiophenyl, benzofuryl, quinoline or isoquinoline, where these heteroaromatic rings are unsubstituted or substituted by C1-C4-alkyl, C1-C4-haloalkyl, C1-C4-alkoxy, C1-C4-alkylthio, halogen, hydroxyl, cyano, formyl, or C1-C4-alkoxycarbonyl, A is a phenyl substituted by C1-C4-haloalkyl and R1, R2, R3, R4 and R5 are hydrogen.

In another group of preferred compounds of the formula I, B is a phenyl, substituted by 1 to 3 substituents, independently selected from cyano, halogen, C1-C4-alkyl, C3-C6-cycloalkyl, C1-C4-haloalkyl-C3-C6-cycloalkyl, C1-C4-haloalkyl and C1-C4-haloalkoxy, A is a phenyl, furyl, pyridyl, pyrimidinyl, pyrazinyl or pyridazinyl, which rings can be unsubstituted or substituted by 1 to 3 substituents, independently selected from C1-C4-alkyl, C1-C4-haloalkyl, C1-C4-alkoxy, C1-C4-haloalkoxy, cyano and halogen, and R1, R2, R3, R4 and R5 are hydrogen. In this group of compounds of formula I, B is especially a phenyl substituted by 1 to 3 substituents, independently selected from fluoro, chloro, bromo, trifluoromethyl and trifluoromethoxy. In this group of compounds of formula I, A is especially a phenyl, pyridyl, pyrazinyl or pyrimidinyl, which rings can be unsubstituted or substituted by 1 to 3 substituents, independently selected from fluoro, methyl and trifluoromethyl.

In another group of preferred compounds of the formula I, B is a phenyl substituted by 1 to 3 substituents, independently selected from fluoro, chloro, trifluoromethyl, cyclopropyl, trifluoromethylcyclopropyl and trifluoromethoxy, A is a phenyl, pyridyl or pyrazinyl, which rings are unsubstituted or substituted by 1 to 3 substituents, independently selected from chloro, bromo, fluoro, methyl, cyano, and trifluoromethyl, and R1, R2, R3, R4 and R5 are hydrogen. More preferably in this group of compounds of formula I, B is especially a phenyl substituted by 1 to 3 substituents, independently selected from fluoro, chloro and trifluoromethoxy, A is especially a phenyl, pyrazinyl or pyridyl, which rings are substituted by 1 to 3 substituents, independently selected from chloro, fluoro, methyl and trifluoromethyl.

In an especially preferred group of compound of formula I, B is phenyl substituted by 1 to 3 substituents, independently selected, from halogen, C1-C4-haloalkyl, and C1-C4-haloalkoxy; A is a phenyl, pyridyl or pyrazinyl, which rings are mono-substituted by a halogen or C1-C4-haloalkyl; and R1, R2, R3, R4 and R5 are hydrogen. More preferably in this group of compounds of formula I, B is especially a phenyl substituted by 1 to 2 substituents, independently selected, from fluoro, chloro, trifluoromethyl and trifluoromethoxy; A is especially a phenyl, pyrazinyl or pyridyl, which rings are mono-substituted by substituents from chloro, fluoro or trifluoromethyl.

In a particularly preferred embodiment, a compound of formula I is where B is 1 or 2 halogen substituted phenyl; R1 to R5 are each hydrogen and A is selected from phenyl, pyrazinyl or pyridyl, each of which is mono- or di-, independently of each other, substituted substituents independently selected from halogen and C1-C4-haloalkyl.

Some compounds of formula I are known and described, for example, in US20090093525, WO07134799, EP1388535, WO06122952 and WO06122955.

Some of the compounds of the formula I are novel. The present invention thus provides compounds of the formula Ic

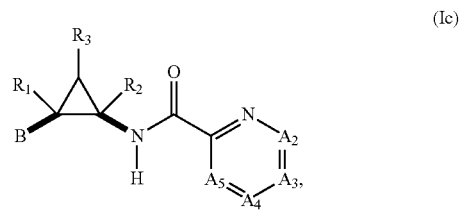

wherein
A2, A3, A4, and A5, independently of each other, are N, CH, or CR11, provided A3 is either CH or N and only one of A2 to A5 is N,
wherein R11 is, independently of each other, halogen, cyano, C1-C4-alkyl, C1-C4-haloalkyl, C1-C4-alkoxy, C1-C4-haloalkoxy, C1-C4-haloalkylthio, C1-C4-alkoxy-C1-C4-alkyl or C1-C4-haloalkoxy-C1-C4-alkyl,
$R_1$, $R_2$ and $R_3$, independently of each other, are hydrogen, halogen, cyano, C1-C4-alkyl or C1-C4-haloalkyl,
B is a mono- or bicyclic 5 to 10 membered heteroaromatic ring system containing 1 to 5 heteroatoms, each independently selected from oxygen, nitrogen and sulphur, or a mono- or bicyclic 5 to 10 membered aromatic ring, wherein the heteroaromatic ring or the aromatic ring is unsubstituted or substituted by R9, where
R9 is, independently of each other, halogen, cyano, R8, —OR8, —C(O)R8, —OC(O)R8, —NR7R8, —NR7C(O) R8, —NR7S(O)nR8, —S(O)nR8, —S(O)nNR7R8, —C(O) OR8 or C(O)NR7R8, where n is 0, 1, or 2,
R7 is, independently of each other, hydrogen, C1-C4-alkyl, C1-C4-haloalkyl, benzyl or phenyl, where benzyl or phenyl is unsubstituted or substituted with halogen, cyano, C1-C4-alkyl or C1-C4-haloalkyl, and
R8 is, independently of each other, C1-C4-alkyl, which is unsubstituted or substituted by R10, C3-C6-cycloalkyl, which is unsubstituted or substituted by R10, C6-C14-bicycloalkyl, which is unsubstituted or substituted by R10, C2-C4-alkenyl, which is unsubstituted or substituted by R10, C2-C4-alkynyl, which is unsubstituted or substituted by R10, phenyl, which is unsubstituted or substituted by R10, or heteroaryl, which is unsubstituted or substituted by R10, where R10 is, independently of each other, hydroxyl, halogen, cyano, C1-C4-alkyl, C1-C4-haloalkyl, C1-C4-alkoxy, C1-C4-haloalkoxy, C1-C4-alkylthio, C1-C4-haloalkylthio, C2-C4-alkenyloxy, C2-C4-alkynyloxy, formyl, C1-C4-alkylcarbonyl, C1-C4alkoxycarbonyl or halophenyl,
wherein B and A-CO—NR5 are cis to each other on the cyclopropyl ring, and tautomers, isomers, enantiomers of these compounds.

Examples of six membered ring —N-A2-A3-A4-A5-C— (corresponding to 'A' in formula I) are 2-pyridyl, 2-pyrimidinyl, 2-pyrazinyl and 2-pyridazinyl, which can be unsubstituted or substituted by one to two substituents independently selected from halogen, cyano, C1-C4-alkyl, C1-C4-haloalkyl, C1-C4-alkoxy, C1-C4-haloalkoxy, C1-C4-haloalkylthio, C1-C4-alkoxy-C1-C4-alkyl and C1-C4-haloalkoxy-C1-C4-alkyl.

Preferably, A4 is, N or CH.

Preferably, A3 is CH.

Preferably A2, A4 and A5 are independently selected from CH or CR11, wherein R11 is independently selected from halogen, cyano, C1-C4-alkyl, or C1-C4-haloalkyl, Preferably, A2 or A5 is CR11, where R11 is preferably, halogen, C1- or C2-haloalkyl or C1- or C2-haloalkoxy, and, more preferably, R11 is fluoro, chloro, bromo, methyl or trifluoromethyl.

Preferred examples of A, independent of other embodiments, are 3-trifluoromethyl-2-pyridyl (A3); 3-methyl-2-pyridyl (A11); 3-methyl-2-pyrazinyl (A24); 3-bromo-2-pyrazinyl (A25); and 3-trifluoromethyl-2-pyrazinyl (A26).

Particularly preferred A independent of other embodiments, is selected from 3-trifluoromethyl-2-pyridyl (A3); 3-methyl-2-pyrazinyl (A24); 3-bromo-2-pyrazinyl (A25); and 3-trifluoromethyl-2-pyrazinyl (A26).

Especially preferred A, independent of other embodiments, is selected from 3-trifluoromethyl-2-pyridyl (A3); and 3-trifluoromethyl-2-pyrazinyl (A26).

Preferably, R1, R2, and R3 are, independently of each other, hydrogen, halogen, C1-C4-alkyl or C1-C4-haloalkyl. In an embodiment, independent of other embodiments, R1, R2, and R3 are each hydrogen.

B is preferably a 5 to 10 membered mono- or bi-cyclic ring system, which may contain 1 or 2 heteroatoms, independently selected, from nitrogen, oxygen and sulphur, which ring system is substituted by substituents (R9). In an instance, there are 1 to 3 substituents R9 on B. Preferably substituent R9, independently from each other, is selected from halogen, cyano, C1-C4-alkyl, C1-C4-haloalkyl, C1-C4-haloalkoxy, C3-C6-cyclopropyl, C1-C4-haloalkyl-C3-C6-cycloalkyl, C1-C4-alkylthio, C1-C4-haloalkylthio, C1-C4-alkylsulfonyl, C1-C4-haloalkylsulfonyl, C1-C4-alkylsulfoxide, C1-C4-haloalkylsulfoxide, benzyloxy, a heteroaryl selected from pyridyl, pyridyloxy, pyrimidinyl, pyridazinyl, pyrazinyl, imidazolyl, pyrazolyl, pyrrolyl, thienyl, benzylthiophenyl, oxazolyl, quinolinyl, isoquinolinyl, furyl or benzofuryl, which is unsubstituted or can have 1 to 3 substituents, independently selected, from halogen, cyano, hydroxyl, C1-C4-alkyl, C1-C4-haloalkyl, C1-C4-alkoxy, C1-C4-alkylthio, formyl, acetyl, and C1-C4-alkoxycarbonyl.

In an embodiment, independent of other embodiments, B is a phenyl substituted 1 to 3 substiutents, independently selected, from halogen, cyano, C1-C4-alkyl, C1-C4-haloalkyl, C1-C4-haloalkoxy, C3-C6-cycloalkyl and C1-C4-haloalkyl-C3-C6-cycloalkyl. In a preferred embodiment, the substitutents are independently selected from bromo, chloro, fluoro, trifluoromethyl, difluoromethoxy, trifluoromethoxy and cyclopropyl.

In a group of preferred compounds of the formula Ic, B is a phenyl, which is unsubstituted or substituted by halogen, cyano, C1-C4-haloalkyl, C1-C4-haloalkoxy, cyclopropyl, imidazolyl, pyrazolyl, C1-C4-alkylthio, C1-C4-alkylsulfoxide, C1-C4-alkylsulfonyl, C1-C4-haloalkylthio, C1-C4-haloalkylsulfoxide or C1-C4-haloalkylsulfonyl, A is 2-pyridyl, 2-pyrimidinyl, 2-pyridazinyl, or 2-pyrazinyl, where these rings are unsubstituted, or mono or di-substituted, independently of each other, by C1-C4-alkyl, C1-C4-alkoxy, C1-C4-haloalkoxy, C1-C4-haloalkyl or halogen, and R1, R2, and R3 are hydrogen. More preferably, in this group of compounds, B is phenyl substituted by halogen, cyano, C1-C4-haloalkyl or C1-C4-haloalkoxy, A is 2-pyridyl, or 2-pyrazinyl, each of which, independently, can be unsubstituted, or mono or di-substituted by substiutents independently selected from C1-C4-alkyl, C1-C4-alkoxy, C1-C4-haloalkoxy, C1-C4-haloalkyl and halogen, and R1, R2, and R3 are hydrogen.

In another group of preferred compounds of the formula Ic, B is a phenyl or pyridyl, which are unsubstituted or substituted by halogen or haloalkoxy, A is 2-pyridyl or 2-pyrazinyl, each of which, independently, can be unsubstituted, or mono or di-substituted by substiutents independently selected from C1-C4-alkyl and C1-C4-haloalkyl, R1 is hydrogen, C1-C4-alkyl or halogen, R3 is hydrogen or C1-C4-alkyl, and R2, is hydrogen.

In another group of preferred compounds of the formula Ic, B is phenyl substituted by furyl, thienyl, pyrazolyl, pyridyl, pyrimidinyl, pyrrolyl, imidazolyl, oxazolyl, benzothiophenyl, benzofuryl, quinoline or isoquinoline, where these heteroaromatic rings are unsubstituted or substituted by C1-C4-alkyl, C1-C4-haloalkyl, C1-C4-alkoxy, C1-C4-alkylthio, halogen, hydroxyl, cyano, formyl, C1-C4-alkoxycarbonyl or halophenyl, A is 2-pyridyl or 2-pyrazinyl, each of which, independently, can be unsubstituted, or mono or di-substituted by substititents independently selected from C1-C4-alkyl, C1-C4-alkoxy, C1-C4-haloalkoxy, C1-C4-haloalkyl and halogen, and R1, R2, and R3 are hydrogen.

In another group of preferred compounds of the formula Ic, B is a phenyl, substituted by 1 to 3 substituents, independently selected from cyano, halogen, C1-C4-alkyl, C3-C6-cycloalkyl, C1-C4-haloalkyl-C3-C6-cycloalkyl, C1-C4-haloalkyl and C1-C4-haloalkoxy, A is 2-pyridyl or 2-pyrazinyl, each of which, independently, can be unsubstituted, or mono or di-substituted by substituents, independently selected, from C1-C4-alkyl, C1-C4-alkoxy, C1-C4-haloalkoxy, C1-C4-haloalkyl and halogen, and R1, R2, and R3 are hydrogen. In this group of compounds of formula Ic, B is especially a phenyl substituted by 1 to 3 substituents, independently selected from fluoro, chloro, bromo, trifluoromethyl and trifluoromethoxy. In this group of compounds of formula Ic, A is especially a 2-pyridyl or 2-pyrazinyl, each of which, independently, can be unsubstituted, or mono or di-substituted by substitutents independently selected from fluoro, methyl and trifluoromethyl.

In another group of preferred compounds of the formula Ic, B is phenyl substituted by 1 to 3 substituents, independently selected from fluoro, chloro, trifluoromethyl, cyclopropyl, trifluoromethylcyclopropyl and trifluoromethoxy, A is 2-pyridyl or 2-pyrazinyl, each of which, independently, can be unsubstituted, or mono or di-substituted by substituents independently selected from chloro, bromo, fluoro, methyl, cyano, and trifluoromethyl, and R1, R2, and R3 are hydrogen. More preferably in this group of compounds of formula Ic, B is especially a phenyl substituted by 1 to 3 substituents, independently selected from fluoro, chloro and trifluoromethoxy, A is especially a 2-pyrazinyl or 2-pyridyl, which rings, independent of each other, are mono or di-substituted by substituents independently selected from chloro, fluoro, methyl and trifluoromethyl.

In an especially preferred group of compound of formula Ic, B is phenyl substituted by 1 to 3 substituents, independently selected, from halogen, C1-C4-haloalkyl, and C1-C4-haloalkoxy; A is 2-pyridyl or 2-pyrazinyl, which rings are mono-substituted, independently of each other, by a halogen or a C1-C4-haloalkyl; and R1, R2, and R3 are hydrogen. More preferably in this group of compounds of formula Ic, B is especially a phenyl substituted by 1 to 2 substituents, independently selected, from fluoro, chloro, trifluoromethyl and trifluoromethoxy; A is especially 2-pyridyl, which rings are mono-substituted by substituents from chloro, fluoro or trifluoromethyl.

In a particularly preferred embodiment, a compound of formula Ic is where B is mono- or di-halogen substituted phenyl; R1 to R3 are each hydrogen and A is selected from 2-pyrazinyl or 2-pyridyl, each of which, independent of each other, is mono- or disubstituted by substituents independently selected from halogen and C1-C4-haloalkyl.

In a group of preferred compounds of the formula Ic, B is phenyl, which is substituted by halogen, cyano, C1-4-haloalkyl, C1-4-haloalkoxy, cyclopropyl, imidazolyl, pyrazolyl, C1-C4-alkylthio, C1-C4-alkylsulfoxide, C1-4-alkylsulfonyl, C1-4-haloalkylthio, C1-4-haloalkylsulfoxide or C1-4-haloalkylsulfonyl, A2 and A4 are, independently of each other, N or CH, A3 is CH and A5 is CR11, where R11 is halogen, C1- or C2-haloalkyl or C1- or C2-haloalkoxy and R1, R2 and R3 are, independently of each other, hydrogen or methyl. More preferably, in this group of compounds, B is phenyl, which is substituted by halogen, C1-C4-haloalkyl or C1-C4-haloalkoxy, A2 and A4 are, independently of each other, N or CH, A3 is CH and A5 is CR11, where R11 is fluoro, chloro, bromo or trifluoromethyl.

In another group of preferred compounds of the formula Ic, B is phenyl or pyridyl, which is substituted by halogen, A2 and A4 are, independently of each other, N or CH, A3 is CH and A5 is CR11, where R11 is halogen, 01- or C2-haloalkyl or 01- or C2-haloalkoxy and R1, R2 and R3 are, independently of each other, hydrogen or methyl. More preferably, R11 is fluoro, chloro, bromo or trifluoromethyl.

In another group of preferred compounds of the formula Ic, B is phenyl substituted by furyl, thienyl, pyrazolyl, pyridyl, pyrimidinyl, pyrrolyl, imidazolyl, oxazolyl, benzothiophenyl, benzofuryl, quinolinyl or isoquinolinyl, where these heteroaromatic rings are unsubstituted or substituted by C1-4 alkyl, C1-C4 haloalkyl, C1-C4-alkoxy, C1-C4-alkylthio, halogen, hydroxyl, cyano, formyl, C1-C4 alkoxycarbonyl or halophenyl, A2 and A4 are, independently of each other, N or CH, A3 is CH and A5 is CR11, where R11 is halogen, 01- or C2-haloalkyl or C1- or C2-haloalkoxy and R1, R2 and R3 are, independently of each other, hydrogen or methyl. More preferably, R11 is fluoro, chloro, bromo or trifluoromethyl.

In another group of preferred compounds of the formula Ic, A5 is CR11, where R11 is fluoro or trifluoromethyl.

Preferably, in respect of each embodiment of the present invention, a compound of formula (I), (Ia), (Ib), (Ic), (Id), or (Ie), is of absolute stereochemistry where B and A-CO—NR5 is in the form of the enantiomer of formula 1ab.

Compounds of formula I, wherein $R_5$ is hydrogen may be prepared according to Scheme 1 by reacting a compound of formula II in which B, $R_1$, $R_2$, $R_3$ and $R_4$ are as defined under formula I; with an acylating agent of formula III in which A is as defined under formula I, and R* is halogen, hydroxyl or C1-C6 alkoxy, preferably chloro, in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

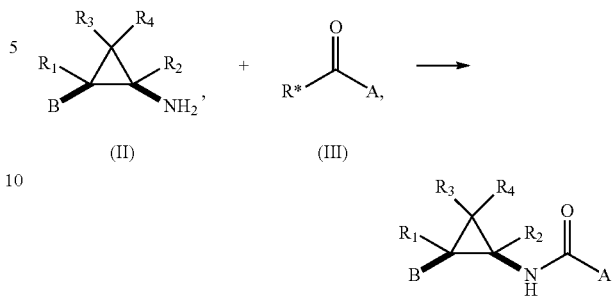

Scheme 1

When R* is hydroxyl, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CD), may be used.

Compounds of the formula Ad can be made according to Scheme 2 by reaction of the enamide (V) with a diazo compound precursor of the formula IVa

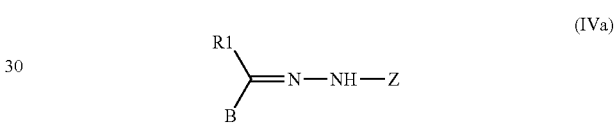

(IVa)

wherein B and R1 are as defined in claim 1 and Z is a leaving group. One example of a compound of formula (IVa) is a compound of formula (IV), where Z is p-tolylSO₂—. Preferred leaving groups Z comprise alkylsulfonyl and arylsulfonyl.

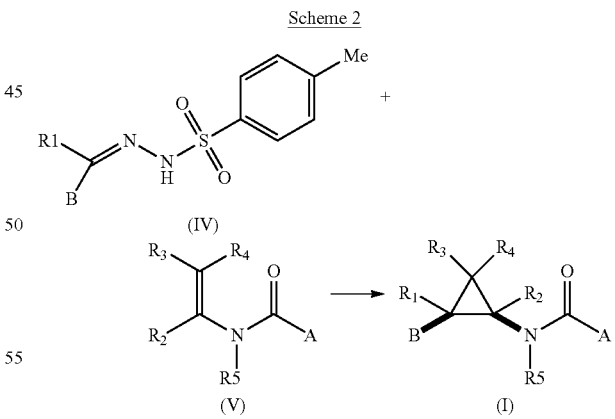

Scheme 2

Certain enamides of the formula V are novel and also part of the present invention. In the compounds of formula Vb, R19 and R20, independently of each other, are hydrogen, halogen, cyano, $C_1$-$C_3$alkyl, $C_1$-$C_3$haloalkyl, with the proviso that at least one of R19 and R20 is not hydrogen. The unsubstituted N-vinyl-benzamide (R19 and R20 are both hydrogen) is known from said Tetrahedron Letters (2008), 49(36), 5255-5257 reference.

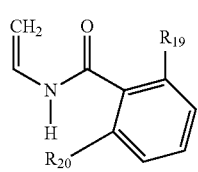

Intermediates of the Formula II (II),

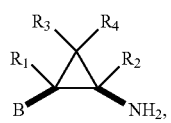

in which B is as defined under formula I, and $R_1$, $R_2$, $R_3$ and $R_4$ are as defined under formula I, may be prepared by reaction Scheme 4, as described in WO 2007/134799.

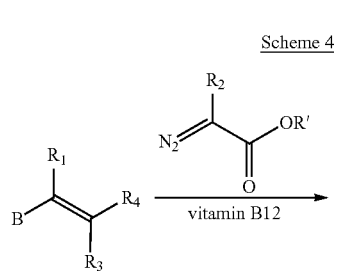

Intermediates of the Formula IIa

in which B is as defined under formula I are intermediates of formula II, in which $R_1$, $R_2$, $R_3$ and $R_4$ are hydrogen and B is as defined under formula I. These may be prepared by reaction Scheme 5 and Scheme 6 as described in WO07134799.

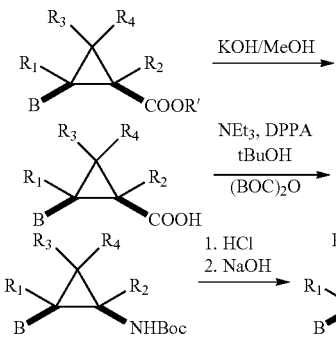

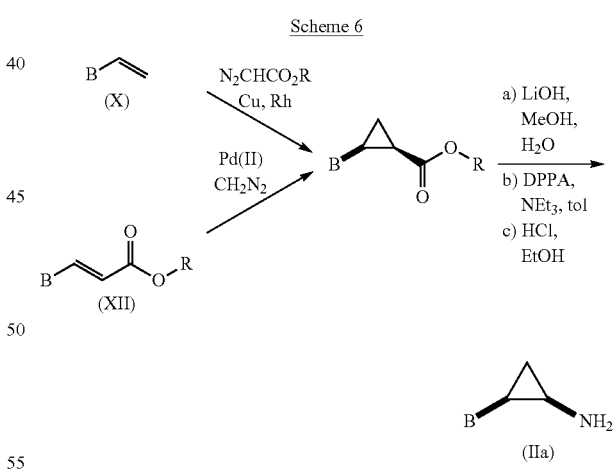

According to Scheme 7, compounds of the formula IIa can also be prepared by deprotecting carbamates of the formula XVII shown below wherein $COOR_{16}$ is a carbamate protecting group. For typical carbamate protecting groups see Greene's Protective Groups in Organic Synthesis, Wiley. Preferred $R_{16}$ is tert.butyl. Carbamates (XVII) can be prepared by reaction of N-vinyl carbamate (XVI) with the sulfonylhydrazone diazo precursor (IV). The N-vinyl carbamate (XVI) can be prepared by alkoxycarbonylation of N-vinylformamide and subsequent deformylation.

Scheme 7

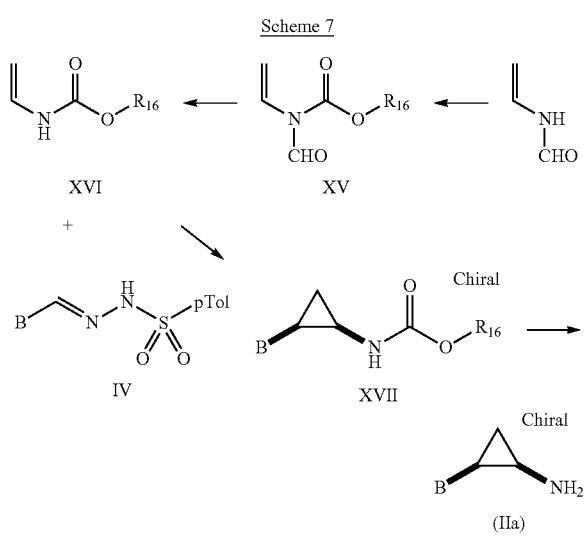

For preparing all further compounds of the formula I functionalized according to the definitions of A, B, $R_1$, $R_2$, $R_3$, $R_4$ and $R_5$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

Compounds of formula Iaa and Iab can be obtained by separation of racemic mixtures of compounds for formula I, for example by chiral chromatography. These reactions can be conveniently performed in a solvent.

These reactions can be conveniently performed at various temperatures.

These reactions can be conveniently performed in an inert atmosphere.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C. A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615 or C. White, Science, vol 318, p. 783, 2007.

It can be advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The invention is further illustrated by making available the following individual compounds of formula (IA) listed below in Tables 1 to 33.

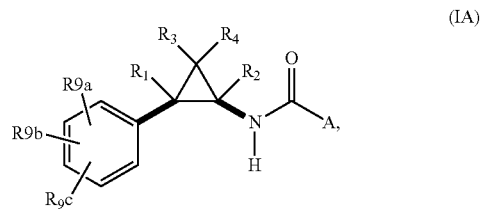

(IA)

Each of Tables 1 to 33, which follow the Table Y below, make available 198 compounds of the formula (IA) in which $R_1$, $R_2$, $R_3$, $R_4$, $R_{9a}$, $R_{9b}$ and $R_{9c}$ are the substituents defined in Table Y and A is the substituent defined in the relevant Table 1 to 33. Thus Table 1 individualises 198 compounds of formula (IA) wherein for each row of Table Y, the A substituent is as defined in Table 1; similarly, Table 2 individualises 198 compounds of formula (IA) wherein for each row of Table Y, the A substituent is as defined in Table 2; and so on for Tables 3 to 33.

TABLE Y

| Compound No. | $R_1$ | $R_2$ | $R_3$ | $R_4$ | $R_{9a}$ | $R_{9b}$ | $R_{9c}$ |
|---|---|---|---|---|---|---|---|
| Y.001 | H | H | H | H | 4-Cl | H | H |
| Y.002 | Me | H | H | H | 4-Cl | H | H |
| Y.003 | nPr | H | H | H | 4-Cl | H | H |
| Y.004 | F | H | H | H | 4-Cl | H | H |
| Y.003 | CN | H | H | H | 4-Cl | H | H |
| Y.004 | CF$_3$ | H | H | H | 4-Cl | H | H |
| Y.005 | H | Me | H | H | 4-Cl | H | H |
| Y.006 | H | nPr | H | H | 4-Cl | H | H |
| Y.007 | H | F | H | H | 4-Cl | H | H |
| Y.008 | H | CN | H | H | 4-Cl | H | H |
| Y.009 | H | CF$_3$ | H | H | 4-Cl | H | H |
| Y.010 | H | Me | Me | H | 4-Cl | H | H |
| Y.011 | H | nPr | nPr | H | 4-Cl | H | H |
| Y.012 | H | F | F | H | 4-Cl | H | H |
| Y.013 | H | CN | CN | H | 4-Cl | H | H |
| Y.014 | H | CF$_3$ | CF$_3$ | H | 4-Cl | H | H |
| Y.015 | H | H | H | Me | 4-Cl | H | H |
| Y.016 | H | H | H | nPr | 4-Cl | H | H |
| Y.017 | H | H | H | F | 4-Cl | H | H |
| Y.018 | H | H | H | CN | 4-Cl | H | H |
| Y.019 | H | H | H | CF$_3$ | 4-Cl | H | H |
| Y.020 | H | H | H | H | 2-Cl | H | H |
| Y.021 | H | H | H | H | 4-OBn | H | H |
| Y.022 | H | H | H | H | 4-F | H | H |
| Y.023 | H | H | H | H | 4-OCHF$_2$ | H | H |
| Y.024 | H | H | H | H | 2-Cl | 4-Br | H |
| Y.025 | H | H | H | H | 2-Cl | 4-Cl | H |
| Y.026 | H | H | H | H | 2-F | 4-Cl | H |
| Y.027 | H | H | H | H | 4-CF3 | H | H |
| Y.028 | H | H | H | H | 3-F | 4-Cl | H |
| Y.029 | H | H | H | H | 4-OCF$_3$ | H | H |
| Y.030 | H | H | H | H | 4-Br | H | H |
| Y.031 | H | H | H | H | 4-CN | H | H |
| Y.032 | H | H | H | H | 2-CF$_3$ | 4-F | H |
| Y.033 | H | H | H | H | 2-Br | 4-F | H |
| Y.034 | H | H | H | H | 4-SMe | H | H |
| Y.035 | H | H | H | H | 4-cPr | H | H |
| Y.036 | H | H | H | H | 4-S(O)Me | H | H |
| Y.037 | H | H | H | H | 4-S(O)2Me | H | H |
| Y.038 | H | H | H | H | 2-F | 4-F | H |
| Y.039 | H | H | H | H | 2-Cl | 4-F | H |
| Y.040 | H | H | H | H | 4-(imidazol-1-yl) | H | H |
| Y.041 | H | H | H | H | 2-F | 4-F | 6-F |
| Y.042 | H | H | H | H | 4-(3-furyl) | H | H |
| Y.043 | H | H | H | H | 4-(3-pyrazolyl) | H | H |

TABLE Y-continued

| Compound No. | R₁ | R₂ | R₃ | R₄ | R₉ₐ | R₉ᵦ | R₉c |
|---|---|---|---|---|---|---|---|
| Y.044 | H | H | H | H | 4-(3-pyridyl) | H | H |
| Y.045 | H | H | H | H | 4-(4-pyridyl) | H | H |
| Y.046 | H | H | H | H | 4-(5-pyrimidinyl) | H | H |
| Y.047 | H | H | H | H | 4-(5-methyl-2-furyl) | H | H |
| Y.048 | H | H | H | H | 4-(3-thienyl) | H | H |
| Y.049 | H | H | H | H | 4-(2-thienyl) | H | H |
| Y.050 | H | H | H | H | 4-(5-formyl-2-furyl) | H | H |
| Y.051 | H | H | H | H | 4-(2-formyl-3-furyl) | H | H |
| Y.052 | H | H | H | H | 4-(3-fluoro-4-pyridyl) | H | H |
| Y.053 | H | H | H | H | 4-(2-fluoro-4-pyridyl) | H | H |
| Y.054 | H | H | H | H | 4-(2-fluoro-3-pyridyl) | H | H |
| Y.055 | H | H | H | H | 4-(2-fluoro-5-pyridyl) | H | H |
| Y.056 | H | H | H | H | 4-(3-methyl-4-thienyl) | H | H |
| Y.057 | H | H | H | H | 4-(2-methoxy-5-pyridyl) | H | H |
| Y.058 | H | H | H | H | 4-(2-methoxy-3-pyridyl) | H | H |
| Y.059 | H | H | H | H | 4-(2-methoxy-5-pyrimidinyl) | H | H |
| Y.060 | H | H | H | H | 4-(2,4-dihydroxy-5-pyrimidinyl) | H | H |
| Y.061 | H | H | H | H | 4-(2-formyl-3-thienyl) | H | H |
| Y.062 | H | H | H | H | 4-(2-formyl-5-thienyl) | H | H |
| Y.063 | H | H | H | H | 4-(2,5-dimethyl-3-thienyl) | H | H |
| Y.064 | H | H | H | H | 4-(6-chloro-3-pyridyl) | H | H |
| Y.065 | H | H | H | H | 4-(2-chloro-3-pyridyl) | H | H |
| Y.066 | H | H | H | H | 4-(2-chloro-4-pyridyl) | H | H |
| Y.067 | H | H | H | H | 4-(3-chloro-5-pyridyl) | H | H |
| Y.068 | H | H | H | H | 4-(5-chloro-2-pyridyl) | H | H |
| Y.069 | H | H | H | H | 4-(2,6-difluoro-3-pyridyl) | H | H |
| Y.070 | H | H | H | H | 4-(2-benzofuryl) | H | H |
| Y.071 | H | H | H | H | 4-(2-chloro-3-thienyl) | H | H |
| Y.072 | H | H | H | H | 4-(2-ethoxy-5-pyridyl) | H | H |
| Y.073 | H | H | H | H | 4-(2-methylthio-5-pyridyl) | H | H |
| Y.074 | H | H | H | H | 4-(1-acetyl-5-thienyl) | H | H |
| Y.075 | H | H | H | H | 4-(2-methylthio-5-pyrimidinyl) | H | H |
| Y.076 | H | H | H | H | 4-(2-chloro-3-methyl-5-pyridyl) | H | H |
| Y.077 | H | H | H | H | 4-(4-isoquinolyl) | H | H |
| Y.078 | H | H | H | H | 4-(2-fluoro-3-chloro-4-pyridyl) | H | H |
| Y.079 | H | H | H | H | 4-(2-benzothiophenyl) | H | H |
| Y.080 | H | H | H | H | 4-(3-benzothiophenyl) | H | H |
| Y.081 | H | H | H | H | 4-(2,6-dimethoxy-3-pyridyl) | H | H |
| Y.082 | H | H | H | H | 4-(2-methoxy-3-chloro-4-pyridyl) | H | H |
| Y.083 | H | H | H | H | 4-(2,2-difluoro-5-methoxy-6-pyridyl) | H | H |
| Y.084 | H | H | H | H | 4-(2-trifluoromethyl-5-pyridyl) | H | H |
| Y.085 | H | H | H | H | 4-(2-fluoro-3-quinolyl) | H | H |
| Y.086 | H | H | H | H | 4-(2,3-difluoro-4-pyridyl) | H | H |
| Y.087 | H | H | H | H | 4-(2,5-dichloro-3-pyridyl) | H | H |
| Y.088 | H | H | H | H | 4-(2,3-dichloro-4-pyridyl) | H | H |
| Y.089 | H | H | H | H | 4-(2,6-dichloro3-pyridyl) | H | H |
| Y.090 | H | H | H | H | 4-(3-pyrrolyl) | H | H |
| Y.091 | H | H | H | H | 4-(2-pyrrolyl) | H | H |
| Y.092 | H | H | H | H | 4-(4-pyrazolyl) | H | H |
| Y.093 | H | H | H | H | 4-(5-oxazolyl) | H | H |
| Y.094 | H | H | H | H | 4-(2,5-dichloro-3-thienyl) | H | H |
| Y.095 | H | H | H | H | 4-(1-methyl-4-pyrazolyl) | H | H |
| Y.096 | H | H | H | H | 4-(1-methyl-5-pyrazolyl) | H | H |
| Y.097 | H | H | H | H | 4-(1-methyl-2-pyrrolyl) | H | H |
| Y.098 | H | H | H | H | 4-(5-formyl-4-methyl-2-thienyl) | H | H |
| Y.099 | H | H | H | H | 4-(1-t.butoxycarbonyl-2-pyrrolyl) | H | H |
| Y.100 | H | H | H | H | 4-(2-(4-fluorophenyl)-5-pyridyl) | H | H |
| Y.101 | H | H | H | H | 4-(2-methyl-4-pyridyl) | H | H |
| Y.102 | H | H | H | H | 4-(1,2-dimethyl-5-imidazolyl) | H | H |
| Y.103 | H | H | H | H | 4-(1-ethyl-4-pyrazolyl) | H | H |
| Y.104 | H | H | H | H | 4-(2-methyl-3-thienyl) | H | H |
| Y.105 | H | H | H | H | 4-(2-cyano-6-pyridyl) | H | H |
| Y.106 | H | H | H | H | 4-(2-cyano-5-methyl-3-furanyl) | H | H |
| Y.107 | H | H | H | H | 4-(1,3,5-trimethyl-4-pyrazolyl) | H | H |
| Y.108 | H | H | H | H | 4-(4-chloro-3-pyridyl) | H | H |
| Y.109 | H | H | H | H | 4-(3-Chloro-4-pyridyl) | H | H |
| Y.110 | H | H | H | H | 4-methyl | H | H |
| Y.111 | H | H | H | H | 4-cyclopentyl | H | H |
| Y.112 | Me | H | H | H | 4-allyl | H | H |
| Y.113 | nPr | H | H | H | 4-propargyl | H | H |
| Y.114 | F | H | H | H | 4-(4-chloro-phenyl) | H | H |
| Y.115 | CN | H | H | H | 4-(3,5-dichloro-pyrid-2yl) | H | H |
| Y.116 | CF₃ | H | H | H | 4-methoxy | H | H |
| Y.117 | H | Me | H | H | 4-cyclopentyloxy | H | H |
| Y.118 | H | nPr | H | H | 4-allyloxy | H | H |
| Y.119 | H | F | H | H | 4-propargyloxy | H | H |
| Y.120 | H | H | H | H | 4-(4-chloro-phenyl)oxy | H | H |

TABLE Y-continued

| Compound No. | R₁ | R₂ | R₃ | R₄ | R_{9a} | R_{9b} | R_{9c} |
|---|---|---|---|---|---|---|---|
| Y.121 | H | H | H | H | 4-(3,5-dichloro-pyrid-2yl)oxy | H | H |
| Y.122 | H | H | H | H | 4-methoxy-carbonyl | H | H |
| Y.123 | H | H | H | H | 4-cyclopentyl-oxycarbonyl | H | H |
| Y.124 | H | H | H | H | 4-allyl-oxycarbonyl | H | H |
| Y.125 | H | H | H | H | 4-propargyl-oxycarbonyl | H | H |
| Y.126 | H | H | H | H | 4-(4-chloro-phenyl)-oxycarbonyl | H | H |
| Y.127 | H | Me | H | H | 4-(3,5-dichloro-pyrid-2yl)-oxycarbonyl | H | H |
| Y.128 | H | nPr | H | H | 4-methylamino | H | H |
| Y.129 | H | F | H | H | 4-cyclopentylamino | H | H |
| Y.130 | H | CN | H | H | 4-allylamino | H | H |
| Y.131 | H | CF₃ | H | H | 4-propargylamino | H | H |
| Y.132 | H | H | Me | H | 4-(4-chloro-phenyl)-amino | H | H |
| Y.133 | H | H | nPr | H | 4-(3,5-dichloro-pyrid-2yl)-amino | H | H |
| Y.134 | H | H | F | H | 4-methyl-N-phenylamino | H | H |
| Y.135 | H | H | H | H | 4-cyclopentyl-N-phenylamino | H | H |
| Y.136 | H | H | H | H | 4-allyl-N-phenylamino | H | H |
| Y.137 | H | H | H | H | 4-propargyl-N-phenylamino | H | H |
| Y.138 | H | H | H | H | 4-(4-chloro-phenyl)-N-phenylamino | H | H |
| Y.139 | H | H | H | H | 4-(3,5-dichloro-pyrid-2yl)-N-phenylamino | H | H |
| Y.140 | H | H | H | H | 4-methyl-N-methylamino | H | H |
| Y.141 | H | H | Me | H | 4-cyclopentyl-N-methylamino | H | H |
| Y.142 | H | H | nPr | H | 4-allyl-N-methylamino | H | H |
| Y.143 | H | H | F | H | 4-propargyl-N-methylamino | H | H |
| Y.144 | H | H | CN | H | 4-(4-chloro-phenyl)-N-methylamino | H | H |
| Y.145 | H | H | CF₃ | H | 4-(3,5-dichloro-pyrid-2yl)-N-methylamino | H | H |
| Y.146 | H | H | H | Me | 4-methyl-aminocarbonyl | H | H |
| Y.147 | H | H | H | nPr | 4-cyclopentyl-aminocarbonyl | H | H |
| Y.148 | H | H | H | F | 4-allyl-aminocarbonyl | H | H |
| Y.149 | H | H | H | H | 4-propargyl-aminocarbonyl | H | H |
| Y.150 | H | H | H | H | 4-(4-chloro-phenyl)-aminocarbonyl | H | H |
| Y.151 | H | H | H | H | 4-(3,5-dichloro-pyrid-2yl)-aminocarbonyl | H | H |
| Y.152 | H | H | H | H | 4-methyl-N-methylaminocarbonyl | H | H |
| Y.153 | H | H | H | H | 4-cyclopentyl-N-methylaminocarbonyl | H | H |
| Y.154 | H | H | H | H | 4-allyl-N-methylaminocarbonyl | H | H |
| Y.155 | H | H | H | H | 4-propargyl-N-methylaminocarbonyl | H | H |
| Y.156 | H | H | H | H | 4-(4-chloro-phenyl)-N-methylaminocarbonyl | H | H |
| Y.157 | H | H | H | H | 4-(3,5-dichloro-pyrid-2yl)-N-methylaminocarbonyl | H | H |
| Y.158 | H | H | H | H | 4-methyl aminosulfonyl | H | H |
| Y.159 | Me | H | H | H | 4-cyclopentyl aminosulfonyl | H | H |
| Y.160 | nPr | H | H | H | 4-allyl aminosulfonyl | H | H |
| Y.161 | F | H | H | H | 4-propargyl aminosulfonyl | H | H |
| Y.162 | CN | H | H | H | 4-(4-chloro-phenyl) aminosulfonyl | H | H |
| Y.163 | CF₃ | H | H | H | 4-(3,5-dichloro-pyrid-2yl) aminosulfonyl | H | H |
| Y.164 | H | Me | H | H | 4-methyl sulfonyl | H | H |
| Y.165 | H | nPr | H | H | 4-cyclopentyl sulfonyl | H | H |
| Y.166 | H | F | H | H | 4-allyl sulfonyl | H | H |
| Y.167 | H | H | H | H | 4-propargyl sulfonyl | H | H |
| Y.168 | H | H | H | H | 4-(4-chloro-phenyl) sulfonyl | H | H |
| Y.169 | H | Me | H | H | 4-(3,5-dichloro-pyrid-2yl) sulfonyl | H | H |
| Y.170 | H | nPr | H | H | 4-methyl sulfonylamino | H | H |
| Y.171 | H | F | H | H | 4-cyclopentyl sulfonylamino | H | H |
| Y.172 | H | CN | H | H | 4-allyl sulfonylamino | H | H |
| Y.173 | H | CF₃ | H | H | 4-propargyl sulfonylamino | H | H |
| Y.174 | H | H | Me | H | 4-(4-chloro-phenyl) sulfonylamino | H | H |
| Y.175 | H | H | nPr | H | 4-(3,5-dichloro-pyrid-2yl) sulfonylamino | H | H |
| Y.176 | H | H | F | H | 4-methylsulfonyl-N-methylamino | H | H |
| Y.177 | H | H | H | H | 4-cyclopentylsulfonyl-N-methylamino | H | H |
| Y.178 | H | H | H | H | 4-allylsulfonyl-N-methylamino | H | H |
| Y.179 | H | H | H | H | 4-propargylsulfonyl-N-methylamino | H | H |
| Y.180 | H | H | H | H | 4-(4-chloro-phenyl) sulfonyl-N-methylamino | H | H |
| Y.181 | H | H | H | H | 4-(3,5-dichloro-pyrid-2yl) sulfonyl-N-methylamino | H | H |
| Y.182 | H | H | H | H | 4-acetoxy | H | H |
| Y.183 | H | H | H | H | 4-cyclopentylcarbonyloxy | H | H |
| Y.184 | H | H | H | H | 4-allylcarbonyloxy | H | H |
| Y.185 | H | H | H | H | 4-propargyl-carbonyloxy | H | H |
| Y.186 | H | H | H | H | 4-(4-chloro-phenyl) carbonyloxy | H | H |
| Y.187 | H | H | H | H | 4-(3,5-dichloro-pyrid-2yl) carbonyloxy | H | H |
| Y.188 | H | H | Me | H | 4-acetamido | H | H |
| Y.189 | H | H | nPr | H | 4-cyclopentylcarbonylamino | H | H |
| Y.190 | H | H | F | H | 4-allylcarbonylamino | H | H |
| Y.191 | H | H | CN | H | 4-propargylcarbonylamino | H | H |
| Y.192 | H | H | CF₃ | H | 4-(4-chloro-phenyl) carbonylamino | H | H |
| Y.193 | H | H | H | Me | 4-(3,5-dichloro-pyrid-2yl) carbonylamino | H | H |
| Y.194 | H | H | Me | H | 4-F | H | H |
| Y.195 | H | Me | H | H | 4-F | H | H |
| Y.196 | H | H | H | H | 4-SCF3 | H | H |

TABLE Y-continued

| Compound No. | $R_1$ | $R_2$ | $R_3$ | $R_4$ | $R_{9a}$ | $R_{9b}$ | $R_{9c}$ |
|---|---|---|---|---|---|---|---|
| Y.197 | H | H | H | H | 4-S(O)2CF3 | H | H |
| Y.198 | H | H | H | H | 4-(pyrazol-1-yl) | H | H |

Table 1 provides 198 compounds of formula (IA), wherein A is 2,6-difluorophenyl (A1), and $R_1$, $R_2$, $R_3$, $R_4$, $R_{9a}$, $R_{9b}$ and $R_{9c}$ are as defined in each row of Table Y. For example, compound 1.001 has the following structure:

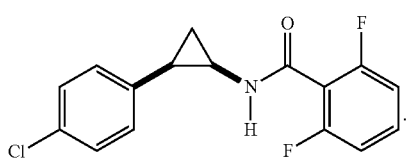

(1.001)

Table 2 provides 198 compounds of formula (IA) wherein A is 2-chloro-3-pyrazinyl (A2) and $R_1$, $R_2$, $R_3$, $R_4$, $R_{9a}$, $R_{9b}$ and $R_{9c}$ are as defined in each row of Table Y.

Table 3 provides 198 compounds of formula (IA) wherein A is 3-trifluoromethyl-2-pyridyl (A3) and $R_1$, $R_2$, $R_3$, $R_4$, $R_{9a}$, $R_{9b}$ and $R_{9c}$ are as defined in each row of Table Y.

Table 4 provides 198 compounds of formula (IA) wherein A is 3-chloro-2-pyridyl (A4) and $R_1$, $R_2$, $R_3$, $R_4$, $R_{9a}$, $R_{9b}$ and $R_{9c}$ are as defined in each row of Table Y.

Table 5 provides 198 compounds of formula (IA) wherein A is 2-trifluoromethyl-3-pyridyl (A5) and $R_1$, $R_2$, $R_3$, $R_4$, $R_{9a}$, $R_{9b}$ and $R_{9c}$ are as defined in each row of Table Y.

Table 6 provides 198 compounds of formula (IA) wherein A is 2-trifluoromethyl-phenyl (A6) and $R_1$, $R_2$, $R_3$, $R_4$, $R_{9a}$, $R_{9b}$ and $R_{9c}$ are as defined in each row of Table Y.

Table 7 provides 198 compounds of formula (IA) wherein A is 2-chloro-3-pyridyl (A7) and $R_1$, $R_2$, $R_3$, $R_4$, $R_{9a}$, $R_{9b}$ and $R_{9c}$ are as defined in each row of Table Y.

Table 8 provides 198 compounds of formula (IA) wherein A is 2-fluoro-6-trifluoromethyl-phenyl (A8) and $R_1$, $R_2$, $R_3$, $R_4$, $R_{9a}$, $R_{9b}$ and $R_{9c}$ are as defined in each row of Table Y.

Table 9 provides 198 compounds of formula (IA) wherein A is 2-tolyl (A9) and $R_1$, $R_2$, $R_3$, $R_4$, $R_{9a}$, $R_{9b}$ and $R_{9c}$ are as defined in each row of Table Y.

Table 10 provides 198 compounds of formula (IA) wherein A is 2-pyrimidinyl (A10) and $R_1$, $R_2$, $R_3$, $R_4$, $R_{9a}$, $R_{9b}$ and $R_{9c}$ are as defined in each row of Table Y.

Table 11 provides 198 compounds of formula (IA) wherein A is 3-methyl-2-pyridyl (A11) and $R_1$, $R_2$, $R_3$, $R_4$, $R_{9a}$, $R_{9b}$ and $R_{9c}$ are as defined in each row of Table Y.

Table 12 provides 198 compounds of formula (IA) wherein A is 2-fluorophenyl (A12) and $R_1$, $R_2$, $R_3$, $R_4$, $R_{9a}$, $R_{9b}$ and $R_{9c}$ are as defined in each row of Table Y.

Table 13 provides 198 compounds of formula (IA) wherein A is 2-chlorophenyl (A13) and $R_1$, $R_2$, $R_3$, $R_4$, $R_{9a}$, $R_{9b}$ and $R_{9c}$ are as defined in each row of Table Y.

Table 14 provides 198 compounds of formula (IA) wherein A is 2-bromophenyl (A14) and $R_1$, $R_2$, $R_3$, $R_4$, $R_{9a}$, $R_{9b}$ and $R_{9c}$ are as defined in each row of Table Y.

Table 15 provides 198 compounds of formula (IA) wherein A is 2-iodophenyl (A15) and $R_1$, $R_2$, $R_3$, $R_4$, $R_{9a}$, $R_{9b}$ and $R_{9c}$ are as defined in each row of Table Y.

Table 16 provides 198 compounds of formula (IA) wherein A is 2,6-dichlorophenyl (A16) and $R_1$, $R_2$, $R_3$, $R_4$, $R_{9a}$, $R_{9b}$ and $R_{9c}$ are as defined in each row of Table Y.

Table 17 provides 198 compounds of formula (IA) wherein A is 2-chloro-6-fluoro-phenyl (A17) and $R_1$, $R_2$, $R_3$, $R_4$, $R_{9a}$, $R_{9b}$ and $R_{9c}$ are as defined in each row of Table Y.

Table 18 provides 198 compounds of formula (IA) wherein A is 2,4,6-trifluorophenyl (A18) and $R_1$, $R_2$, $R_3$, $R_4$, $R_{9a}$, $R_{9b}$ and $R_{9c}$ are as defined in each row of Table Y.

Table 19 provides 198 compounds of formula (IA) wherein A is 2-trifluoromethoxy-phenyl (A19) and $R_1$, $R_2$, $R_3$, $R_4$, $R_{9a}$, $R_{9b}$ and $R_{9c}$ are as defined in each row of Table Y.

Table 20 provides 198 compounds of formula (IA) wherein A is 2-fluoro-6-methyl-phenyl (A20) and $R_1$, $R_2$, $R_3$, $R_4$, $R_{9a}$, $R_{9b}$ and $R_{9c}$ are as defined in each row of Table Y.

Table 21 provides 198 compounds of formula (IA) wherein A is 2-fluoro-6-methoxy-phenyl (A21) and $R_1$, $R_2$, $R_3$, $R_4$, $R_{9a}$, $R_{9b}$ and $R_{9c}$ are as defined in each row of Table Y.

Table 22 provides 198 compounds of formula (IA) wherein A is 2-methyl-3-pyridyl (A22) and $R_1$, $R_2$, $R_3$, $R_4$, $R_{9a}$, $R_{9b}$ and $R_{9c}$ are as defined in each row of Table Y.

Table 23 provides 198 compounds of formula (IA) wherein A is 3-fluoro-2-pyridyl (A23) and $R_1$, $R_2$, $R_3$, $R_4$, $R_{9a}$, $R_{9b}$ and $R_{9c}$ are as defined in each row of Table Y.

Table 24 provides 198 compounds of formula (IA) wherein A is 3-methyl-2-pyrazinyl (A24) and $R_1$, $R_2$, $R_3$, $R_4$, $R_{9a}$, $R_{9b}$ and $R_{9c}$ are as defined in each row of Table Y.

Table 25 provides 198 compounds of formula (IA) wherein A is 3-bromo-2-pyrazinyl (A25) and $R_1$, $R_2$, $R_3$, $R_4$, $R_{9a}$, $R_{9b}$ and $R_{9c}$ are as defined in each row of Table Y.

Table 26 provides 198 compounds of formula (IA) wherein A is 3-trifluoromethyl-2-pyrazinyl (A26) and $R_1$, $R_2$, $R_3$, $R_4$, $R_{9a}$, $R_{9b}$ and $R_{9c}$ are as defined in each row of Table Y.

Table 27 provides 198 compounds of formula (IA) wherein A is 2-methyl-3-furyl (A27) and $R_1$, $R_2$, $R_3$, $R_4$, $R_{9a}$, $R_{9b}$ and $R_{9c}$ are as defined in each row of Table Y.

Table 28 provides 198 compounds of formula (IA) wherein A is 5-chloro-4-pyrimidinyl (A28) and $R_1$, $R_2$, $R_3$, $R_4$, $R_{9a}$, $R_{9b}$ and $R_{9c}$ are as defined in each row of Table Y.

Table 29 provides 198 compounds of formula (IA) wherein A is 2-cyanophenyl (A29) and $R_1$, $R_2$, $R_3$, $R_4$, $R_{9a}$, $R_{9b}$ and $R_{9c}$ are as defined in each row of Table Y.

Table 30 provides 198 compounds of formula (IA) wherein A is 2-trifluoromethylthio-phenyl (A30) and $R_1$, $R_2$, $R_3$, $R_4$, $R_{9a}$, $R_{9b}$ and $R_{9c}$ are as defined in each row of Table Y.

Table 31 provides 198 compounds of formula (IA) wherein A is 3-(difluoromethyl)-1-methyl-pyrazol-4-yl (A31) and $R_1$, $R_2$, $R_3$, $R_4$, $R_{9a}$, $R_{9b}$ and $R_{9c}$ are as defined in each row of Table Y.

Table 32 provides 198 compounds of formula (IA) wherein A is 3-(trifluoromethyl)-1-methyl-pyrazol-4-yl (A32) and $R_1$, $R_2$, $R_3$, $R_4$, $R_{9a}$, $R_{9b}$ and $R_{9c}$ are as defined in each row of Table Y.

Table 33 provides 198 compounds of formula (IA) wherein A is 2-fluoro-3-pyridyl (A33) and $R_1$, $R_2$, $R_3$, $R_4$, $R_{9a}$, $R_{9b}$ and $R_{9c}$ are as defined in each row of Table Y The invention is further illustrated by making available the following individual compounds of formula (IB) listed below in Tables 34 to 66.

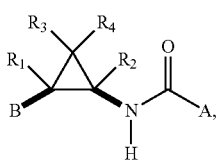

(IB)

Each of Tables 34 to 66, which follow the Table Z below, make available 84 compounds of the formula (IB) in which $R_1$, $R_2$, $R_3$, $R_4$, and B are the substituents defined in Table Z and A is the substituent defined in the relevant Table 34 to 66. Thus Table 34 individualises 84 compounds of formula (IB) wherein for each row of Table Z, the A substituent is as defined in Table 34; similarly, Table 35 individualises 84 compounds of formula (IB) wherein for each row of Table Z, the A substituent is as defined in Table 35; and so on for Tables 36 to 66.

TABLE Z

| Compound No. | $R_1$ | $R_2$ | $R_3$ | $R_4$ | B |
|---|---|---|---|---|---|
| Z.001 | H | H | H | H | 3-chloro-5-trifluoromethyl-2-pyridyl |
| Z.002 | Me | H | H | H | 3-chloro-5-trifluoromethyl-2-pyridyl |
| Z.003 | nPr | H | H | H | 3-chloro-5-trifluoromethyl-2-pyridyl |
| Z.004 | F | H | H | H | 3-chloro-5-trifluoromethyl-2-pyridyl |
| Z.005 | CN | H | H | H | 3-chloro-5-trifluoromethyl-2-pyridyl |
| Z.006 | $CF_3$ | H | H | H | 3-chloro-5-trifluoromethyl-2-pyridyl |
| Z.007 | H | Me | H | H | 3-chloro-5-trifluoromethyl-2-pyridyl |
| Z.008 | H | nPr | H | H | 3-chloro-5-trifluoromethyl-2-pyridyl |
| Z.009 | H | F | H | H | 3-chloro-5-trifluoromethyl-2-pyridyl |
| Z.010 | H | CN | H | H | 3-chloro-5-trifluoromethyl-2-pyridyl |
| Z.011 | H | $CF_3$ | H | H | 3-chloro-5-trifluoromethyl-2-pyridyl |
| Z.012 | H | Me | Me | H | 3-chloro-5-trifluoromethyl-2-pyridyl |
| Z.013 | H | nPr | nPr | H | 3-chloro-5-trifluoromethyl-2-pyridyl |
| Z.014 | H | F | F | H | 3-chloro-5-trifluoromethyl-2-pyridyl |
| Z.015 | H | CN | CN | H | 3-chloro-5-trifluoromethyl-2-pyridyl |
| Z.016 | H | $CF_3$ | $CF_3$ | H | 3-chloro-5-trifluoromethyl-2-pyridyl |
| Z.017 | H | H | H | Me | 3-chloro-5-trifluoromethyl-2-pyridyl |
| Z.018 | H | H | H | nPr | 3-chloro-5-trifluoromethyl-2-pyridyl |
| Z.019 | H | H | H | F | 3-chloro-5-trifluoromethyl-2-pyridyl |
| Z.020 | H | H | H | CN | 3-chloro-5-trifluoromethyl-2-pyridyl |
| Z.021 | H | H | H | $CF_3$ | 3-chloro-5-trifluoromethyl-2-pyridyl |
| Z.022 | H | H | H | H | 3-chloro-5-trifluoromethyl-2-pyridyl |
| Z.023 | H | H | H | H | 2-fluoro-5-chloro-3-pyridyl |
| Z.024 | H | H | H | H | 3,5-dichloro-2-pyridyl |
| Z.025 | H | H | H | H | 3-fluoro-5-chloro-2-pyridyl |
| Z.026 | H | H | H | H | 3,5-dichloro-2-pyridyl |
| Z.027 | H | H | H | H | 2-chloro-4-pyridyl |
| Z.028 | H | H | H | H | 2-chloro-4-pyrimidinyl |
| Z.029 | H | H | H | H | 5-chloro-2-pyrimidinyl |
| Z.030 | H | H | H | H | 4-chloro-3-pyridazinyl |
| Z.031 | H | H | H | H | 4-trifluoromethyl-3-pyridazinyl |
| Z.032 | H | H | H | H | 2-chloro-5-pyridazinyl |
| Z.033 | H | H | H | H | 2-trifluoromethyl-5-pyridazinyl |
| Z.034 | H | H | H | H | 6-chloro-sym-triazin-2-yl |
| Z.035 | H | H | H | H | 5-chloro-2-thienyl |
| Z.036 | H | H | H | H | 4-chloro-2-thienyl |
| Z.037 | H | H | H | H | 5-trifluoromethyl-2-thienyl |
| Z.038 | H | H | H | H | 5-chloro-3-thienyl |
| Z.039 | H | H | H | H | 4-chloro-3-thienyl |
| Z.040 | H | H | H | H | 5-chloro-2-thiazolyl |
| Z.041 | H | H | H | H | 2-trifluoromethyl-4-thiazolyl |
| Z.042 | H | H | H | H | 5-chloro-3-isothiazolyl |
| Z.043 | H | H | H | H | 1,2,3 thiadiazol-4-yl |
| Z.044 | H | H | H | H | 5-chloro-2-furyl |
| Z.045 | H | H | H | H | 4-chloro-2-furyl |
| Z.046 | H | H | H | H | 5-trifluoromethyl-2-furyl |
| Z.047 | H | H | H | H | 5-chloro-3-furyl |
| Z.048 | H | H | H | H | 4-chloro-3-furyl |
| Z.049 | H | H | H | H | 5-chloro-2-oxazolyl |
| Z.050 | H | H | H | H | 2-trifluoromethyl-4-oxazolyl |
| Z.051 | H | H | H | H | 5-chloro-3-isoxazolyl |

TABLE Z-continued

| Compound No. | $R_1$ | $R_2$ | $R_3$ | $R_4$ | B |
|---|---|---|---|---|---|
| Z.052 | H | H | H | H | 1,2,3 oxaadiazol-4-yl |
| Z.053 | H | H | H | H | 4-chloro-2-pyrrolyl |
| Z.054 | H | H | H | H | 1-methyl-3-chloro-2-pyrrolyl |
| Z.055 | H | H | H | H | 4-chloro-3-pyrazolyl |
| Z.056 | H | H | H | H | 1-methyl-4-chloro-3-pyrazolyl |
| Z.057 | H | H | H | H | 4-chloro-2-imidazolyl |
| Z.058 | H | H | H | H | 1-methyl-5-chloro-2-imidazolyl |
| Z.059 | H | H | H | H | 1,2,4-triazol-2-yl |
| Z.060 | H | H | H | H | 1,2,4-triazol-1-yl |
| Z.061 | H | H | H | H | 1-methyl-1,2,3-triazol-4-yl |
| Z.062 | H | H | H | H | 4-chloro-1,2,3-triazol-1-yl |
| Z.063 | H | H | H | H | 4-chloro-1-naphthyl |
| Z.064 | H | H | H | H | 5-cyano-2-naphthyl |
| Z.065 | H | H | H | H | 7-trifluoromethyl-1-naphthyl |
| Z.066 | H | H | H | H | 3-methylsulfonyl-1-naphthyl |
| Z.067 | H | H | H | H | 6-acetamido-2-naphthyl |
| Z.068 | H | H | H | H | 8-chloro-4-quinolizinyl |
| Z.069 | H | H | H | H | 6-chloro-1-quinolinyl |
| Z.070 | H | H | H | H | 5-allylamino-4-quinolinyl |
| Z.071 | H | H | H | H | 7-chloro-1-isoquinolyl |
| Z.072 | H | H | H | H | 8-cyano-4-quinazolyl |
| Z.073 | H | H | H | H | 6-trifluoromethyl-3-cinnolinyl |
| Z.074 | H | H | H | H | 3-bromo-2-quinoxalinyl |
| Z.075 | H | H | H | H | 6-allylamino-4-phthalazinyl |
| Z.076 | H | H | H | H | 4-pteridinyl |
| Z.077 | H | H | H | H | 3-methylsulfonyl-2-benzofuryl |
| Z.078 | H | H | H | H | 6-chloro-3-isobenzofuryl |
| Z.079 | H | H | H | H | 5-cyano-2-benzoxazolyl |
| Z.080 | H | H | H | H | 6-cyano-3-benzothiobphenyl |
| Z.081 | H | H | H | H | 4-methylthio-2-benzthiazolyl |
| Z.082 | H | H | H | H | 2-fluoro-5-benzimidazolyl |
| Z.083 | H | H | H | H | 6-chloro-7-purinyl |
| Z.084 | H | H | H | H | 2-fluoro-5-chloro-3-pyridyl |

Table 34 provides 84 compounds of formula (IB), wherein A is 2,6-difluorophenyl (A1) and $R_1$, $R_2$, $R_3$, $R_4$, and B are as defined in each row of Table Z. For example, compound 34.001 has the following structure.

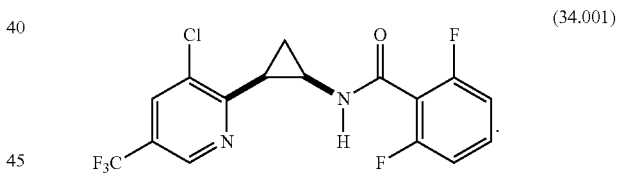

(34.001)

Table 35 provides 84 compounds of formula (IB) wherein A is 2-chloro-3-pyrazinyl (A2) and $R_1$, $R_2$, $R_3$, $R_4$, and B are as defined in each row of Table Z.

Table 36 provides 84 compounds of formula (IB) wherein A is 3-trifluoromethyl-2-pyridyl (A3) and $R_1$, $R_2$, $R_3$, $R_4$, and B are as defined in each row of Table Z.

Table 37 provides 84 compounds of formula (IB) wherein A is 3-chloro-2-pyridyl (A4) and $R_1$, $R_2$, $R_3$, $R_4$, and B are as defined in each row of Table Z.

Table 38 provides 84 compounds of formula (IB) wherein A is 2-trifluoromethyl-3-pyridyl (A5) and $R_1$, $R_2$, $R_3$, $R_4$, and B are as defined in each row of Table Z.

Table 39 provides 84 compounds of formula (IB) wherein A is 2-trifluoromethyl-phenyl (A6) and $R_1$, $R_2$, $R_3$, $R_4$, and B are as defined in each row of Table Z.

Table 40 provides 84 compounds of formula (IB) wherein A is 2-chloro-3-pyridyl (A7) and $R_1$, $R_2$, $R_3$, $R_4$, and B are as defined in each row of Table Z.

Table 41 provides 84 compounds of formula (IB) wherein A is 2-fluoro-6-trifluoromethyl-phenyl (A8) and $R_1$, $R_2$, $R_3$, $R_4$, and B are as defined in each row of Table Z.

Table 42 provides 84 compounds of formula (IB) wherein A is 2-tolyl (A9) and $R_1$, $R_2$, $R_3$, $R_4$, and B are as defined in each row of Table Z.

Table 43 provides 84 compounds of formula (IB) wherein A is 2-pyrimidinyl (A10) and $R_1$, $R_2$, $R_3$, $R_4$, and B are as defined in each row of Table Z.

Table 44 provides 84 compounds of formula (IB) wherein A is 3-methyl-2-pyridyl (A11) and $R_1$, $R_2$, $R_3$, $R_4$, and B are as defined in each row of Table Z.

Table 45 provides 84 compounds of formula (IB) wherein A is 2-fluorophenyl (A12) and $R_1$, $R_2$, $R_3$, $R_4$, and B are as defined in each row of Table Z.

Table 46 provides 84 compounds of formula (IB) wherein A is 2-chlorophenyl (A13) and $R_1$, $R_2$, $R_3$, $R_4$, and B are as defined in each row of Table Z.

Table 47 provides 84 compounds of formula (IB) wherein A is 2-bromophenyl (A14) and $R_1$, $R_2$, $R_3$, $R_4$, and B are as defined in each row of Table Z.

Table 48 provides 84 compounds of formula (IB) wherein A is 2-iodophenyl (A15) and $R_1$, $R_2$, $R_3$, $R_4$, and B are as defined in each row of Table Z.

Table 49 provides 84 compounds of formula (IB) wherein A is 2,6-dichlorophenyl (A16) and $R_1$, $R_2$, $R_3$, $R_4$, and B are as defined in each row of Table Z.

Table 50 provides 84 compounds of formula (IB) wherein A is 2-chloro-6-fluoro-phenyl (A17) and $R_1$, $R_2$, $R_3$, $R_4$, and B are as defined in each row of Table Z.

Table 51 provides 84 compounds of formula (IB) wherein A is 2,4,6-trifluorophenyl (A18) and $R_1$, $R_2$, $R_3$, $R_4$, and B are as defined in each row of Table Z.

Table 52 provides 84 compounds of formula (IB) wherein A is 2-trifluoromethoxy-phenyl (A19) and $R_1$, $R_2$, $R_3$, $R_4$, and B are as defined in each row of Table Z.

Table 53 provides 84 compounds of formula (IB) wherein A is 2-fluoro-6-methyl-phenyl (A20) and $R_1$, $R_2$, $R_3$, $R_4$, and B are as defined in each row of Table Z.

Table 54 provides 84 compounds of formula (IB) wherein A is 2-fluoro-6-methoxy-phenyl (A21) and $R_1$, $R_2$, $R_3$, $R_4$, and B are as defined in each row of Table Z.

Table 55 provides 84 compounds of formula (IB) wherein A is 2-methyl-3-pyridyl (A22) and $R_1$, $R_2$, $R_3$, $R_4$, and B are as defined in each row of Table Z.

Table 56 provides 84 compounds of formula (IB) wherein A is 3-fluoro-2-pyridyl (A23) and $R_1$, $R_2$, $R_3$, $R_4$, and B are as defined in each row of Table Z.

Table 57 provides 84 compounds of formula (IB) wherein A is 3-methyl-2-pyrazinyl (A24) and $R_1$, $R_2$, $R_3$, $R_4$, and B are as defined in each row of Table Z.

Table 58 provides 84 compounds of formula (IB) wherein A is 3-chloro-2-pyrazinyl (A25) and $R_1$, $R_2$, $R_3$, $R_4$, and B are as defined in each row of Table Z.

Table 59 provides 84 compounds of formula (IB) wherein A is 3-trifluoromethyl-2-pyrazin (A26) and $R_1$, $R_2$, $R_3$, $R_4$, and B are as defined in each row of Table Z.

Table 60 provides 84 compounds of formula (IB) wherein A is 2-methyl-3-furyl (A27) and $R_1$, $R_2$, $R_3$, $R_4$, and B are as defined in each row of Table Z.

Table 61 provides 84 compounds of formula (IB) wherein A is 5-chloro-4-pyrimidinyl (A28) and $R_1$, $R_2$, $R_3$, $R_4$, and B are as defined in each row of Table Z.

Table 62 provides 84 compounds of formula (IB) wherein A is 2-cyanophenyl (A29) and $R_1$, $R_2$, $R_3$, $R_4$, and B are as defined in each row of Table Z.

Table 63 provides 84 compounds of formula (IB) wherein A is 2-trifluoromethylthio-phenyl (A30) and $R_1$, $R_2$, $R_3$, $R_4$, and B are as defined in each row of Table Z.

Table 64 provides 84 compounds of formula (IB) wherein A is 3-(difluoromethyl)-1-methyl-pyrazol-4-yl (A31) $R_1$, $R_2$, $R_3$, $R_4$, and B are as defined in each row of Table Z.

Table 65 provides 84 compounds of formula (IB) wherein A is 3-(trifluoromethyl)-1-methyl-pyrazol-4-yl (A32) and $R_1$, $R_2$, $R_3$, $R_4$, and B are as defined in each row of Table Z.

Table 66 provides 84 compounds of formula (IB) wherein A is 2-fluoro-3-pyridyl (A33) $R_1$, $R_2$, $R_3$, $R_4$, and B are as defined in each row of Table Z.

Examples of formula (VI) made available are those where the substitutent A in formula (VI) correspond to any one of A1 to A33.

It has now been found that the compounds of formula I according to the invention have, for practical purposes, a very advantageous spectrum of activities for protecting animals and useful plants against attack and damage by nematodes.

The compounds of formula (I), including formula (Ic), are especially useful for the control of nematodes. Thus, in a further aspect, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Particularly, the nematode species *Meloidogyne* spp., *Heterodera* spp., *Rotylenchus* spp. and *Pratylenchus* spp. can be controlled by compounds of the invention.

A compound of formula (Ic) may also be found to control the damage caused by a pest and/or fungi.

In an embodiment, a compound of formula (Ic) can be used in agriculture.

Accordingly, the invention is moreover directed to a method of controlling damage and/or yield loss caused by a pest and/or fungi which comprises applying to a pest, to a locus of a pest, or to a plant susceptible to attack by a pest and/or fungi or to a plant propagation material an effective amount of a compound of formula (Ic).

The compounds according to the invention can be used for controlling, i.e. containing or destroying, pests and/or fungi which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests.

The compounds of formula (Ic) according to the invention are preventively and/or curatively valuable active ingredients in the field of pest control, even at low rates of application, which can be used against pesticide resistant pests and fungi, which compounds of formula (Ic) have a very favorable biocidal spectrum and are well tolerated by warm-blooded species, fish and plants.

The compounds according to the invention may act against all or individual developmental stages of normally sensitive, but also resistant, animal pests, such as insects or representatives of the order Acarina. The insecticidal or acaricidal activity of the compounds according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

In an embodiment, the compounds of the invention of formula (Ic) may also have activity against other pests (such as insects) and fungi.

Examples of animal pests are:
from the order Acarina, for example,
*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp., *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,
*Haematopinus* spp., *Linognathus* spp., *Pediculus* spp., *Pemphigus* spp. and *Phylloxera* spp.;

from the order Coleoptera, for example,
*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremmus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp., *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp;

from the order Diptera, for example,
*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,
*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

from the order homoptera, for example,
*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,
*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example,

*Lepisma saccharina.*

In a further aspect, the invention may also relate to a method of controlling or preventing infestation of useful plants by phytopathogenic microorganisms, wherein a compound of formula (I) is applied as active ingredient to the plants, to parts thereof or the locus thereof. The compounds of formula (I) according to the invention are distinguished by activity, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different useful plants, while at the same time protecting also those parts of the plants that grow later e.g. from phytopathogenic microorganisms. It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Examples of fungi include: Fungi imperfecti (e.g. *Botrytis, Pyricularia, Helminthosporium, Fusarium, Septoria, Cercospora* and *Alternaria*); Basidiomycetes (e.g. *Rhizoctonia, Hemileia, Puccinia*); the Ascomycetes classes (e.g. *Venturia* and *Erysiphe, Podosphaera, Monilinia, Uncinula*); Oomycetes classes (e.g. *Phytophthora, Pythium, Plasmopara*); Zygomycetes (e.g., *Rhizopus* spp.); family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal plants and *Puccinia recondita*, also known as brown rust.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia* controversa or *Tilletia* indica), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* form a specie tritici), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;—barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* form a specie hordei), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Plrytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding plants, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing plants, for example rape, as regards controlling the following seed diseases: *Phoma lingam, Alternaria brassicae* and *Sclerotinia sclerotiorum*;

corn, as regards controlling seed diseases: (*Rhizopus* sp., *Penicillium* sp., *Trichoderma* sp., *Aspergillus* sp., and *Gibber ellafujikuroi*);

flax, as regards controlling the seed disease: *Alternaria linicola*;

forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous plants, as regards controlling the following diseases of seeds or of young plants grown from seeds: damping-off and collar rot (*Fusarium oxysporum, Fusarium roseum, Rhizoctonia solani, Pythium* sp.);

leguminous plants, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: *monilia* disease (*Monilia fructigenae, M. laxa*), scab (*Venturia inaequalis*), powdery mildew (*Podosphaera leucotricha*);—vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beticola*), leaf spot (*Ramularia beticola*).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

The following list of pesticides together with which the compounds according to the invention can be used, is intended to illustrate the possible combinations by way of example.

The following combination of the compounds of formula (I) with another active compounds are preferred (the abbreviation "TX" means "one compound selected from any one of Tables 1 to 66 of the present invention":

an adjuvant selected from the group of substances consisting of petroleum oils (alternative name) (628)+TX, an acaricide selected from the group of substances consisting of 1,1-bis(4-chloro-phenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fen-pyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, flupyradifurone+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfuram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and yl-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name)(347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (254)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Pasteuria penetrans*+TX, *Pasteuria thornei*+TX, *Pasteuria nishizawae*+TX, *Pasteuria ramosa*+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B₁ (alternative name) (839)+TX, trimedlure B₂ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl)ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-s-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl o-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code)

(1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, yl-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-5-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesamolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0)+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6] +TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7] +TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1] +TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3] +TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5] +TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-5-methyl [135158-54-2]+TX, anilazine [101-05-3]+TX, benthiavalicarb [413615-35-7]+TX, blasticidin-S [2079-00-7] +TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7] +TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfo-carb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1] +TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)$_5$-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, and 3-difluoromethyl-1-methyl-1H-pyrazole-4-carboxylic acid (3',4',5'-trifluoro-biphenyl-2-yl)-amide (disclosed in WO 2006/087343)+TX.

The references in square brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address: http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The mass ratio of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:1 to 1:100, including from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5, for example 1:3 to 3:1. The mixing ratios are understood to include, on the one hand, ratios by mass and also, on other hand, molar ratios.

Examples of application methods for the compounds of the invention amd compositions thereof, that is the methods of controlling pests/fungi in the agriculture, are spraying, atomizing, dusting, brushing on, dressing, scattering or pouring— which are to be selected to suit the intended aims of the prevailing circumstances.

A preferred method of application in agriculture is application to the foliage of the plants (foliar application), it being possible to select frequency and rate of application to match the danger of infestation with the pest/fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddyfield.

Typical rates of application per hectare is generally 1 to 2000 g of active ingredient per hectare, in particular 10 to 1000 g/ha, preferably 10 to 600 g/ha, such as 50 to 300 g/ha.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

Suitable target plants are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, amd lawn grass or turf).

In an embodiment, the plant is selected from cereals, corn, soybean, rice, sugarcane, vegetables and oil plants.

The term "plant" is to be understood as including also plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins from Bacillus cereus or Bacillus popilliae; or insecticidal proteins from Bacillus thuringiensis, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic plants are:
1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a Cry1Ab toxin. Bt176 maize also transgenically expresses the enzyme PAT to achieve tolerance to the herbicide glufosinate ammonium.
3. MIR604Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from Agrobacterium sp. strain CP4, which imparts tolerance to the herbicide Roundup® (contains glyphosate), and also a Cry1Ab toxin obtained from Bacillus thuringiensis subsp. kurstaki which brings about tolerance to certain Lepidoptera, include the European corn borer.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematocides, plant activators, acaricides, and insecticides.

Accordingly, the present invention also makes available a composition comprising a compound of the invention and an agronomicaly carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

Examples of compositions for use in agriculture are emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—a compound according to the invention and the type of composition is to be selected to suit the intended aims and the prevailing circumstances.

Examples of suitable liquid carriers are unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Examples of solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates and Flowable Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

Formulation Examples

%=Percent by Weight

Example F1

Emulsion Concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9

Powders for Dry Seed Treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10

Emulsifiable Concentrate

| active ingredient | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11

Flowable Concentrate for Seed Treatment

| active ingredients | 40% |
|---|---|
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Examples of foliar formulation types for pre-mix compositions are:
  GR: Granules
  WP: wettable powders
  WG: water dispersable granules (powders)
  SG: water soluble granules SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50, %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

A compound of the formula (I) is in a preferred embodiment, independent of any other embodiments, is in the form of a plant propagation material treating (or protecting) composition, wherein said plant propagation material protecting composition comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

The combinations of the present invention (i.e. those comprising a compound of the present invention and one or more other biological active agents) may be applied simulatenously or sequentially.

In the event, the ingredients of a combination are applied sequentially (i.e., one after the other), the ingredients are applied sequentially within a reasonable period of each other to attain the biological performance, such as within a few hours or days. The order of applying the ingredients in the combination, i.e., whether the compounds of formula (I) should be applied first or not is not essential for working the present invention.

In the event ingredients of the combinations are applied simultaneously in the present invention, they may be applied as a composition containing the combination, in which case (A) the compound of formula (I) and the one or more other ingredients in the combinations can be obtained from separate formulation sources and mixed together (known as a tank-mix, ready-to-apply, spray broth, or slurry), or (B) the compound of formula (I) and the one or more other ingredients can be obtained as single formulation mixture source (known as a pre-mix, ready-mix, concentrate, or formulated product).

In an embodiment, independent of other embodiments, a compound according to the present invention is applied as a combination. Accordingly, the present invention also provides a composition comprising a compound according the invention as herein described and one or more other biological active agents, and optionally one or more customary formulation auxiliaries; which may be in the form of a tank-mix or pre-mix composition.

Alternative to the actual synergistic action with respect to biological activity, the combinations according to the invention also can have surprising advantageous properties which can also be described, in a wider sense, as synergistic activity. Examples of such advantageous properties that may be mentioned are: advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; or any other advantages familiar to a person skilled in the art.

The compounds of the present invention for use in agriculture is preferably a nematicide.

The compounds of the present invention may also find application in other fields, such as one or more of protection of stored goods and store rooms, the protection of raw materials (such as wood and textiles), floor coverings and buildings, and in hygiene management—especially the protection of humans, domestic animals and productive livestock against pests. The invention therefore also makes available pesticidal compositions for such uses and the methods therefor. The composition would need to be modified for use in a particular use, and a skilled person would be able to make available such compositions for any particular use.

In the hygiene sector, the compositions according to the invention are active against ectoparasites such as hard ticks, soft ticks, mange mites, harvest mites, flies (biting and licking), parasitic fly larvae, lice, hair lice, bird lice and fleas. Examples of such parasites are Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The application methods for applying a compound or a composition thereof to stored goods, store rooms, raw materials (such as wood and textiles), floor coverings and buildings, and in hygiene management is known in the art.

The invention also provides a method for treating, curing, controlling, preventing and protecting warm-blooded animals, including humans, and fish against infestation and infection by helminths, arachnids and arthropod endo- and ectoparasites which comprises orally, topically or parenterally administering or applying to said animals an anthelmintically, acaricidally or endo- or ectoparasiticidally effective amount of compound of formula (I).

The above method is particularly useful for controlling and preventing helminth, nemtode, acarid and arthropod endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of invention are especially useful for the control of helminths and nematodes. Examples for helminths are members of the class Trematoda, commonly known as flukes or flatworms, especially members of the genera *Fasciola*, *Fascioloides*, *Paramphistomu*, *Dicrocoelium*, *Eurytrema*, *Ophisthorchis*, *Fasciolopsis*, *Echinostoma* and *Paragonimus*. Nematodes which can be controlled by the formula (I) compounds include the genera *Haemonchus*, *Ostertagia*, *Cooperia*, *Oesphagastomu*, *Nematodirus*, *Dictyocaulus*, *Trichuris*, *Dirofilaria*, *Ancyclostoma*, *Ascaria* and the like.

The compound of this invention may also control endoparasitic arthropod infestations such as cattle grub and stomach bot. In addition, acarid and arthropod ectoparasitic infestations in warm-blooded animals and fish including biting lice, sucking lice, bot flies, biting flies, muscoid flies, flies, myiasitic fly larvae, gnats, mosquitoes, fleas, mites, ticks, nasal bots, keds and chiggers may be controlled, prevented or eliminated by the compounds of this invention. Biting lice include members of Mallophaga such as *Bovicola bovis*, *Trichodectes canis* and *Damilina ovis*. Sucking lice include members of Anoplura such as *Haematopinus eurysternus*, *Haematopinus suis*, *Linognathus vituli* and *Solenopotes capillatus*. Biting flies include members of *Haematobia*. Ticks include *Boophilus*, *Rhipicephalus*, *Ixodes*, *Hyalomma*, *Amblyomma* and *Dermacentor*. The compounds of the invention may also be used to control mites which are parasitic on warm-blooded mammals and poultry including mites of the orders Acariformes and Parasitiformes.

For oral administration to warm-blooded animals, the compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with about 0.01 mg/kg to 100 g/kg of animal body weight per day of the compound of the invention.

Alternatively, the compounds of the invention may be administered to animals parenterally, for example, by intraruminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compounds of the invention may be transdermally administered to animals. For parenteral administration, the dosage form chosen should provide the animal with about 0.01 mg/kg to 100 mg/kg of animal body weight per day of the compound of the invention.

The compounds of the invention may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound of the invention. In addition, the compounds of the invention may be formulated as ear tags for animals, particularly quadrupeds such as cattle and sheep.

The compounds of the invention may also be used in combination or conjunction with one or more other parasiticidal compounds (to broaden the spectrum of activity) including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The parasiticidal compositions of the present invention include a parasiticidally effective amount of a compound of the invention or combinations thereof admixed with one or more physiologically tolerable inert, solid or liquid carriers known from veterinary medicinal practice for oral, percutaneous and topical administration. Such compositions may comprise further additives, such as stabilizers, anifoams, viscosity regulators, binders and tackifiers, whereas commercial products will preferably be formulated as concentrates, the end user will normally employ dilute formulations.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

In an embodiment, independent of any other embodiments, a compound of formula (I) is a anti-helminth compound.

In an embodiment, independent of any other embodiments, a compound of formula (I) is a pesticidal compound, preferably a nematicidal compound.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The disclosure in the present application makes available each and every combination of embodiments disclosed herein.

The following Examples serve to illustrate the invention. They do not limit the invention. Temperatures are given in degrees Celsius; mixing ratios of solvents are given in parts by volume.

EXAMPLES

Preparation Examples

Example P1

Preparation of 3-difluoromethyl-1-methyl-1H-pyrazole-4-carboxylic acid [(cis)-2-(4-fluoro-phenyl)-cyclopropyl]-amide (67.002)

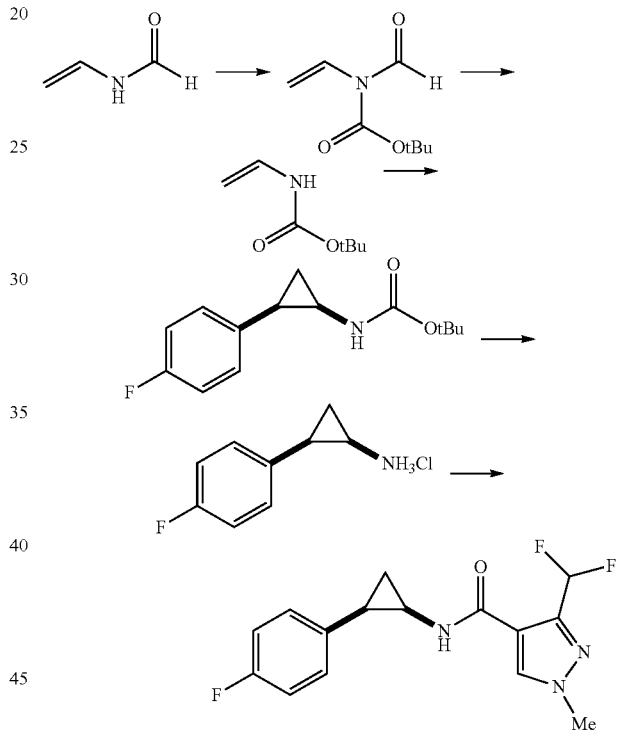

a) Preparation of N-Formyl-N-Vinyl-Carbamic Acid Tert-Butyl Ester

N-Vinylformamide (39.2 ml, 40 g, 563 mmol) and dimethylaminopyridine (3.44 g, 28.1 mmol) were dissolved in THF (100 ml). A solution of $Boc_2O$ (147.4 g, 675.3 mmol) in THF (200 ml) was added. The rate of $CO_2$ production was followed with a bubbler. There was a very small exotherm. The Boc anhydride solution was added at such a rate as to give a strong steady $CO_2$ production. After complete addition the solution was stirred until bubbling nearly stopped (ca 2-3 hours) and left for three days. Ice (ca 500 g) was added and stirred for 15 minutes. The mixture was separated between cyclohexane (1 L) and water (500 ml). The organic phase was washed twice with water, dried with $MgSO_4$, and evaporated, leaving a yellow liquid, which NMR showed to be 89% pure. The only impurity visible in NMR is Boc anhydride (13 mole %).

1H-NMR (CDCl$_3$) 1.55 (9H, s), 5.08 (1H, d), 5.67 (1H, d), 6.60 (1H, dd).

b) Preparation of N-Vinyl-Carbamic Acid Tert-Butyl Ester

A solution of N-formyl-N-vinyl-carbamic acid tert-butyl ester (103.6 g, crude 89% pure, 539 mmol) in THF (320 ml) was cooled to 0° C. and stirred rapidly. NaOH (2M, 323 ml, 6.46 mmol) was slowly added over ca 20 minutes. The internal temperature rose to 19° C., and began then to cool. After cooling to 5° C. the mixture was warmed to RT. After 1 hour the reaction was finished according to tlc and GC. The reaction mixture was shaken between tBuOMe (250 ml) and water (250 ml), washed with water (250 ml) and brine (250 ml), dried over MgSO$_4$ and evaporated. The product was a yellow oil containing traces of THF (NMR). The crude product was dissolved in pentane (25 ml), seeded, and left overnight at −20° C. The colourless crystals were swirled in pentane, filtered off and washed 3× with pentane, then spread in the air to dry to yield 48.9 g (63%). The mother liquors were evaporated down, dissolved in a little pentane and seeded. A further 8.1 g (11%) was isolated. (The product can also be sublimed/distilled.) m.p. 67-68° C.

1H-NMR (CDCl$_3$) 1.47 (9H, s), 4.22 (1H, d), 4.41 (1H, d), 6.33 (1H, bs, NH), 6.68 (1H, ddd).

c) Preparation of Cis-2-(4-Fluoro-Phenyl)-Cyclopropyl-Carbamic Acid Tert-Butyl Ester 4-Fluorophenyl benzaldehyde-tosylhydrazone sodium salt (786 mg, 2.5 mmol), N-vinyl-carbamic acid tert-butyl ester (1.432 g, 10 mmol) and benzyltriethylammonium chloride (57 mg, 0.25 mmol) were covered with dioxane (11 ml) under argon. Rh2(OAc)4 (11 mg, 0.025 mmol) was added and the suspension stirred at room temperature for 15 minutes. The slurry became thick and difficult to stir so a further 4 ml of dioxane was added. The mixture was stirred at 75° C. for 2 hours, then shaken between tBuOMe and water. The organic phase was washed with water and NaCl (satd), dried over MgSO$_4$ and evaporated to yield a brown viscous oil (1.353 g), which was chromatographed on silica to yield 2-(4-fluorophenyl)-cyclopropyl-carbamic acid tert-butyl ester 369 mg (59%, m.p. 117-118° C.) cis and 125 mg (20% m.p. 102-105° C.) trans.

1H-NMR (CDCl$_3$, signals for the cis isomer) 0.93 (1H, m), 1.32 (9H, s), 2.20 (1H, m), 2.89 (1H, m), 4.23 (1H, m), 6.98 (2H, t), 7.18 (2H, t).

d) Preparation of cis-2-(4-fluoro-phenyl)-cyclopropylamine hydrochloride cis-2-(4-Fluoro-phenyl)-cyclopropyl-carbamic acid tert-butyl ester (0.239 g, 0.951 mmol) was dissolved in dichloromethane (5 ml). Under argon HCl (4 M in dioxan, 2.38 ml, 9.5 mmol) was added and the clear solution stirred at room temperature. After 3 hours a precipitate had formed and the reaction was complete according to tlc (30% EtOAc/cyclohexane) and LC/MS. The solvent was evaporated and the residue stirred with tBuOMe. The solid was filtered off and washed twice with tBuOMe and dried to yield 155 mg (87%) of the product as a white solid.

1H-NMR (D6-DMSO) 1.26 (2H, m), 2.35 (1H, m), 2.81 (1H, m), 7.19 (2H, m), 7.40 (2H, m), 8.12 (2H, s, NH$_2$).

e) Preparation of 3-difluoromethyl-1-methyl-1H-pyrazole-4-carboxylic acid [(cis)-2-(4-fluoro-phenyl)-cyclopropyl]-amide cis-2-(4-Fluoro-phenyl)-cyclopropylamine hydrochloride (0.153 g, 0.815 mmol) was dissolved in dichloromethane (4.5 ml) and stirred with NaHCO3 (1 M, 4.5 ml). 3-(difluoromethyl)-1-methyl-1H-pyrazol-4-carbonyl chloride (0.190 g, 0.978 mmol) was added dropwise. After three hours rapid stirring tlc (50% EtOAc/hexane) showed the reaction to be finished. The mixture was separated between dichloromethane and water, washed with NaCl (sat), dried (MgSO$_4$), and evaporated to yield 245 mg of nearly pure product, which was washed with cyclohexane to yield 215 mg (85%) of the product as a white solid m.p. 141-143° C.

1H-NMR (CDCl$_3$) 1.03 (1H, m), 1.42 (1H, m), 2.38 (1H, m), 3.27 (1H, m), 3.85 (3H, N-Me), 5.97 (1H, bs, NH), 6.55 (1H, t), 6.97 (2H, m), 7.21 (2H, m), 7.78 (1H, s).

Example P2

Preparation of N-[cis-2-(4-Fluoro-Phenyl)-Cyclopropyl]-2-Trifluoromethyl-benzamide (67.003)

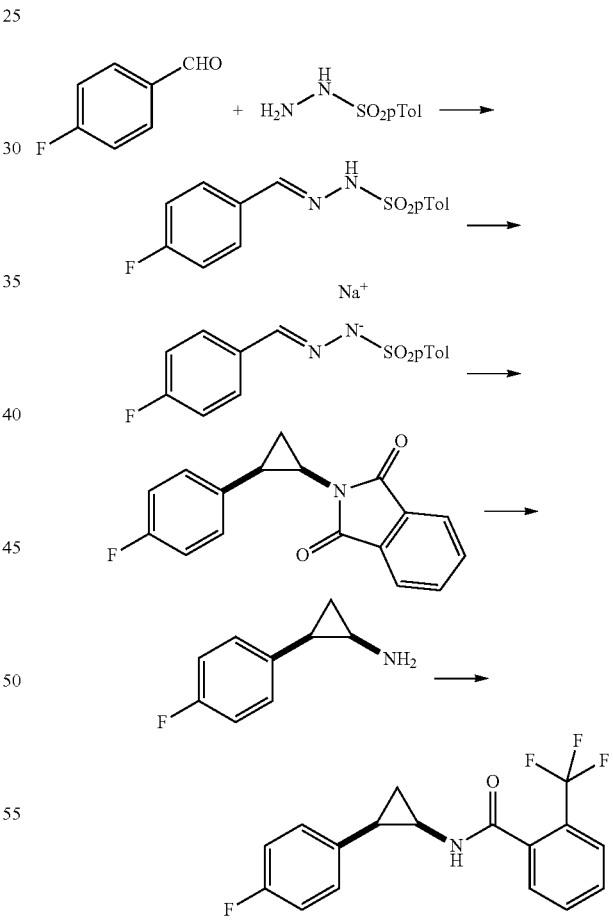

a) Preparation of 4-fluorophenyl benzaldehyde-tosylhydrazone

4-Fluoro-benzaldehyde (26.6 ml, 31.25 g, 251 mmol) was added all at once to a stirred suspension of 4-tolylsulfonyl hydrazine (43.47 g, 287 mmol) in methanol (200 ml). Within 30 seconds everything dissolved and there was a small exotherm to 32° C., before the temperature dropped. After 30 minutes some of the solvent was evaporated. Crystallisation started after scratching and the solution was left for two hours at room temperature and overnight at ca 5° C. to crystallize. The crystals were filtered off, washed with methanol (2×ca 30 ml), then left in the air to dry, yielding 51.8 g (71%) m.p. 123-125° C.

1H-NMR (D6-DMSO) 2.36 (3H, s); 7.22 (2H, dd); 7.42 (2H, d); 5.60 (2H, dd); 7.78 (2H, d); 7.91 (1H, s); 11.45 (s, 1H).

b) Preparation of 4-fluorophenyl benzaldehyde-tosylhydrazone sodium salt

A solution of 30% MeONa in methanol (31.9 ml, 5.4 M, 172 mmol) was dissolved in further methanol (132 ml). Under stirring 4-fluorophenyl benzaldehyde-tosylhydrazone (47.9 g, 164 mmol) was added. After 3 minutes everything had gone into solution. The solvent was evaporated and the solid residue was ground with a pestle in a mortar to yield 46.4 g (90%).

1H-NMR (D6-DMSO) 2.30 (3H, s); 7.02 (2H, dd); 7.13 (2H, d); 7.49 (2H, dd); 7.58 (1H, s); 7.59 (2H, d).

c) Preparation of 2-[cis-2-(4-fluoro-phenyl)-cyclopropyl]-isoindole-1,3-dione 4-Fluorophenyl benzaldehyde-tosylhydrazone sodium salt (1.57 g, 5 mmol), N-vinyl-phthalimide (2.59 g, 15 mmol), benzyltriethylammonium chloride (114 mg, 0.5 mmol), and rhodium acetate dimer (22 mg, 0.05 mmol) were stirred with dioxane (23 ml) to give a thick slurry. This was stirred overnight at room temperature. Tlc (20% EtOAc/hexane) showed good conversion, so the mixture was shaken between EtOAc and water. The organic phase was dried with MgSO4 and evaporated to yield 3.8 g of a crude mixture. This was chromatographed on silica with EtOAc/hexane to yield 169 mg (12%) of 2-[cis-2-(4-fluoro-phenyl)cyclopropyl]-isoindole-1,3-dione $^1$H-NMR (CDCl$_3$) 1.60 (1H, ddd, 7.7, 7.7, 7.7 Hz); 2.19 (1H, ddd, J=7.7, 7.3, 4.9 Hz); 2.51 (ddd, J=7.3, 7.3, 7.3 Hz); 3.08 (1H, ddd, 7.7, 7.7, 4.9 Hz); 6.81 (2H, dd, J=8.8, 8.8 Hz); 7.06 (2H, dd, J=8.8, 5.1); 7.55 (2H, m); 7.61 (2H m).

d) Preparation of cis-2-(4-fluoro-phenyl)-cyclopropylamine

Hydrazine hydrate (0.523 mmol, 0.54 g, 10.6 mmol) was added to a solution of 2-[cis-2-(4-fluoro-phenyl)-cyclopropyl]-isoindole-1,3-dione (500 mg, 1.78 mmol) in dichloromethane (5 ml) and ethanol (1 ml). After 3 hours at room temperature a spongy precipitate had formed. It was filtered off and washed with dichloromethane. The filtrate was evaporated to yield 150 mg of impure product. This was stirred with Et$_2$O and the solid filtered off. Evaporation of the filtrate yielded (37%) of almost pure cis-2-(4-fluoro-phenyl)-cyclopropylamine as an oil.

1H-NMR (CDCl$_3$) 0.72 (1H, m); 1.09 (1H, m); 1.15 (2H, br); 2.00 (1H, m); 2.51 (1H, m); 6.97 (2H, m); 7.20 (2H, m).

e) Preparation of N-[cis-2-(4-fluoro-phenyl)-cyclopropyl]-2-trifluoromethyl-benzamide 2-Trifluoromethylbenzoyl chloride (165 mg, 0.794 mmol) was added to a rapidly stirred mixture of cis-2-(4-fluoro-phenyl)-cyclopropylamine (100 mg, 0.662 mmol) in dichloromethane (2 ml) and NaHCO3 (1 M aq., 1 ml). After one hour at room temperature the mixture was shaken between EtOAc and NaHCO$_3$ (1 M), dried (Na$_2$SO$_4$) and evaporated to yield 205 mg crude product. This was stirred with Et$_2$O and the solid filtered off. The ether was evaporated and stirred with hexane to yield 120 mg of impure product.

A further batch of cis-2-(4-fluoro-phenyl)-cyclopropylamine (1.5 g, 9.93 mmol) was treated in the same way to yield 3.8 g of crude product, which was chromatographed with the 120 mg from above to yield pure N-[cis-2-(4-fluoro-phenyl)-cyclopropyl]-2-trifluoromethyl-benzamide (1.67 g, 52%) m.p. 140-142° C.

1H-NMR (CDCl$_3$) 1.11 (1H, m); 1.46 (1H, m); 2.42 (1H, m); 3.31 (1H, m); 5.38 (1H, br s); 7.00 (2H, m); 7.06 (1H, m); 7.26 (4H, m); 7.45 (2H, m); 7.61 (1H, m).

Example P3

Preparation of N-[cis-2-(4-difluoromethoxy-phenyl)-cyclopropyl]-2-trifluoromethyl-benzamide (67.011)

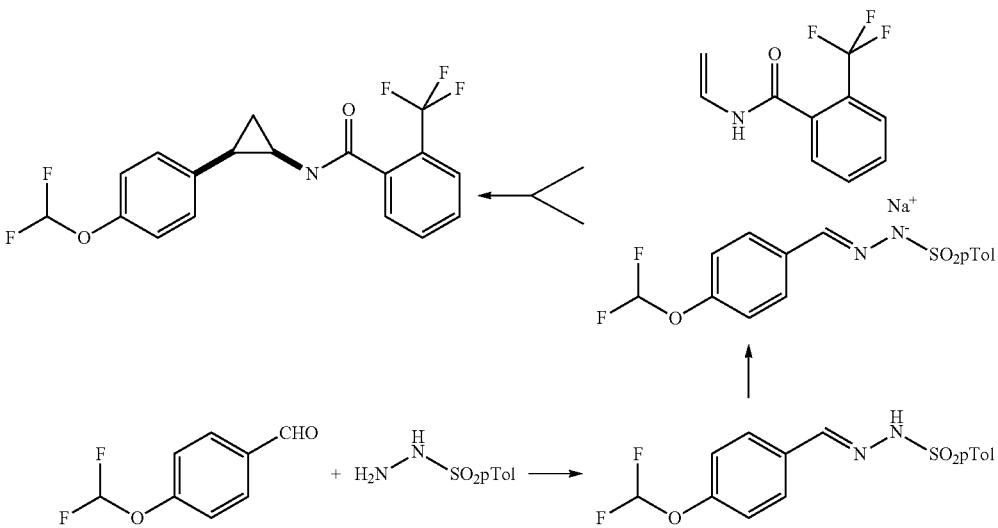

a) Preparation of N-[2-(4-difluoromethoxy-phenyl)-cyclopropyl]-2-trifluoromethyl-benzamide 4-Difluoromethoxy-phenyl benzaldehyde-tosylhydrazone sodium salt (64 mg, 0.177 mmol), 2-trifluoromethyl-N-vinyl-benzamide (152 mg, 0.707 mmol), benzyltriethylammonium chloride (4 mg, 0.018 mmol), and rhodium acetate dimer (0.85 mg, 0.0018 mmol) were stirred with dioxane (0.5 ml) to give a thick slurry. This was stirred overnight at room temperature and then heated at 60° C. for 2 hours. Tlc (30% EtOAc/hexane) showed good conversion, so the mixture was shaken between tBuOMe and water, washed with NaCl (sat.), dried (MgSO$_4$) and evaporated to yield 166 mg of crude product, which was chromatographed with EtOAc/Hexane to yield 24 mg (37%) of a mixture (ca 75:25 of cis:trans)N-[2-(4-difluoromethoxy-phenyl)-cyclopropyl]-2-trifluoromethyl-benzamide as a gum. 1H-NMR (CDCl$_3$, signals for cis-N-[2-(4-difluoromethoxy-phenyl)-cyclopropyl]-2-trifluoromethyl-benzamide) 1.11 (1H, m); 1.45 (1H, m); 2.42 (1H, m); 3.28 (1H, m); 5.43 (1H, br s); 6.47 (1H, d, J=70); 6.95-7.20 (7H, m).

b) Preparation of 4-difluoromethoxy-phenyl benzaldehyde-tosylhydrazone

4-Tolylsulfonyl hydrazine (6.03 g, 182 mmol) was added to a stirred solution of 4-difluoromethoxy-benzaldehyde (5 g, 172 mmol) in methanol (6 ml). Everything dissolved. After two hours the solvent was evaporated to yield 9.8 g (99%) of a white solid.

1H-NMR (D6-DMSO) 2.35 (3H, s); 7.19 (2H, d); 7.29 (1H, t, J=70); 7.39 (2H, d); 7.60 (2H, d); 7.75 (2H, d); 7.92 (1H, s).

c) Preparation of 4-difluoromethoxy-phenyl benzaldehyde-tosylhydrazone sodium salt A solution of 30% MeONa in methanol (2.7 ml, 5.4 M, 15 mmol) was added to a solution of 4-difluoromethoxy-phenyl benzaldehyde-tosylhydrazone (5 g, 14.7 mmol). After one hour the solvent was evaporated and the solid residue was ground with a pestle in a mortar to yield 5.2 g (98%) of the product as a white solid.

1H-NMR (D6-DMSO) 2.28 (3H, s), 6.91 (2H, d); 7.12 (2H, d); 7.13 (1H, t, J=70); 7.38 (2H d); 7.77 (1H, s); 7.78 (2H, d).

Example P4

Preparation of racemic 2,6-difluoro-N-[(1R,2R,3R)-2-(4-fluorophenyl)-3-methyl-cyclopropyl]benzamide (68.003)

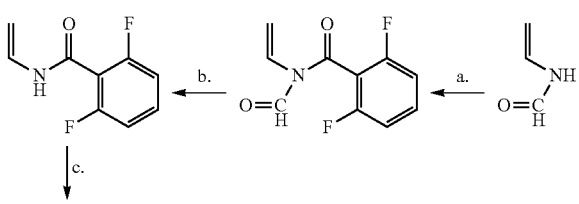

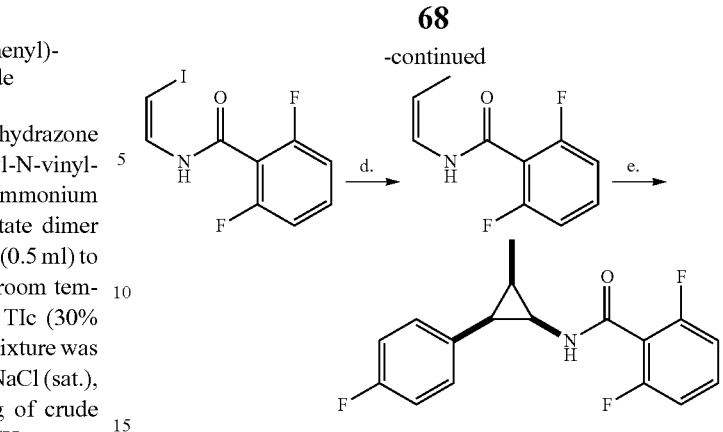

a) Preparation of 2,6-difluoro-N-formyl-N-vinyl-benzamide 2,6-difluorobenzoyl chloride (35.4 ml, 50 g, 284 mmol) was added dropwise with stirring to a solution of N-vinylformamide (18 ml, 18.3 g, 258 mmol), 4-dimethylaminopyridine (3.1 g, 25.8 mmol), and triethylamine (53.8 ml, 39 g, 387 mmol) in dichloromethane (200 ml). The temperature was kept at ca 20° C. with an ice/water bath. After the addition the mixture was stirred two hours at room temperature then shaken between tBuOMe and water. The organic phase was washed with half saturated brine, dried with Na2SO4 and evaporated to give 47 g (87% crude) of 2,6-difluoro-N-formyl-N-vinyl-benzamide, which contained ca 60% of 2,6-difluoro-N-vinyl-benzamide, which is the product of the next step, in which the formyl group has already been cleaved.

1H-NMR (CDCl3) 5.23 (1H, d); 5.60 (1H, d); 6.67 (1H, dd); 7.02 (2H, m); 7.48 (1H, m); 9.08 (1H, s).

b) Preparation of 2,6-difluoro-N-vinyl-benzamide n-Propylamine (36.7 ml, 26.33 g, 444 mmol) was added to a solution of crude 2,6-difluoro-N-formyl-N-vinyl-benzamide from step a (47 g, 222 mmol) in dichloromethane (200 ml). There was a weak exotherm. The reaction mixture was kept at room temperature with a cold water bath. The solution was then concentrated on the rotovap to give a brown oil, which was crystallised from ethanol/water to yield 30 g (75%) of pure 2,6-difluoro-N-vinyl-benzamide as beige crystals. A further 5.7 g was crystallised from concentration of the mother liquors. M.p. 103-107° C.

1H-NMR (CDCl$_3$) 4.58 (1H, d); 4.76 (1H, d); 6.97 (2H, m); 7.14 (1H, m); 7.41 (1H, m); 7.60 (1H, br s, NH).

c) Preparation of 2,6-difluoro-N—[(Z)-2-iodovinyl]benzamide

Triethylamine (4.19 ml, 3.038 g, 30.03 mmol) was added to a solution of 2,6-difluoro-N-vinyl-benzamide (5.0 g, 27.3 mmol) in dichloromethane (ca 40 ml) at 0° C. with stirring. After 10 minutes N-iodosuccinimide (6.147 g, 27.3 mmol) was added. The temperature rose to 15° C. After 5 minutes everything went into solution. After 60 minutes at room temperature the reaction mixture was shaken between tBuOMe and NaHCO3 (1 M), dried with MgSO$_4$, and evaporated to give the crude product mixture (10.07 g). This was chromatographed with EtOAc and cyclohexane to give 4.91 g of the product, which was still a mixture. Further chromatography with dimethoxyethane/hexane yielded 2.81 g (33%) of pure 2,6-difluoro-N—[(Z)-2-iodovinyl]benzamide M.p. 88-90° C.

1H-NMR (CDCl3) 5.57 (1H, d); 7.03 (2H, t); 7.47 (1H, m); 7.54 (1H, m), 7.92 (1H, br s, NH).

The E-isomer and a diiodo compound were also separated from this chromatography.

d) Preparation of 2,6-difluoro-N—[(Z)-prop-1-enyl]benzamide

Zinc bromide (1.68 g, 7.48 mmol) was added in portions to a solution of MeMgBr in diethyl ether (3M, 2.4 ml, 7.23 mmol).After stirring at room temperature there was a thick prepicipitate. Some DMF and THF was added to improve solubility and aid stirring. 2,6-difluoro-N—[(Z)-2-iodovinyl]benzamide (746 mg, 2.41 mmol) was added and then dichloro-bisacetonitrile palladium (12.5 mg, 0.048 mmol) was added, and the mixture stirred overnight at RT and then shaken between diethyl ether and HCl (1 M), dried with MgSO4, evaporated and chromatographed with EtOAc/cyclohexane to yield pure 2,6-difluoro-N—[(Z)-prop-1-enyl]benzamide (406 mg, 86%) m.p. 71-74° C.

1H-NMR (CDCl3) 1.75 (3H, d); 4.99 (1H, dq); 6.92 (1H, dd); 7.00 (2H, m); 7.45 (3H, m).

e) Preparation of racemic 2,6-difluoro-N-[(1R,2R,3R)-2-(4-fluorophenyl)-3-methyl-cyclopropyl]benzamide 4-Fluorophenyl benzaldehyde-tosylhydrazone sodium salt from example P2b (261 mg, 0.832 mmol), 2,6-difluoro-N—[(Z)-prop-1-enyl]benzamide (164 mg, 832 mmol), benzyltriethylammonium chloride (18.6 mg, 0.083 mmol), and rhodium acetate dimer (3.6 mg, 0.0083 mmol) were stirred with dioxane (6 ml) to give a thick slurry. This was heated at 75° C. for 4 hours. The mixture was shaken between EtOAc and water. The organic phase was dried with $MgSO_4$ and evaporated to yield 230 mg of a crude mixture. This was chromatographed on silica with EtOAc/cyclohexane to yield 26 mg (10%) of racemic 2,6-difluoro-N-[(1R,2R,3R)-2-(4-fluorophenyl)-3-methyl-cyclopropyl]benzamide. M.p. 90-96° C.

1H-NMR ($CDCl_3$) 1.06 (3H, d); 1.60 (1H, m); 2.33 (1H, m); 3.55 (1H, m); 5.52 (1H, br s, NH); 6.90 (2H, t); 7.03 (2H, t); 7.26 (2H, m); 7.34 (1H, m).

Example P5

Preparation of racemic N-[(1R,2R)-2-(4-chlorophenyl)-2-methyl-cyclopropyl]-2,6-difluoro-benzamide (68.009)

a) Preparation of cis+trans ethyl 2-(4-chlorophenyl)-2-methyl-cyclopropanecarboxylate A solution of ethyl diazo acetate (5.86 ml, 6.36 g, 50.1 mmol) in benzene was added over 3 hours through a reflux condenser to a mixture of Rh(OAc)2 (222 mg, 0.50 mmol) and 4-chloro-methyl styrene (10 ml, 10.8 g, 60.1 mmol) which was stirred in an oil bath, which was kept at 90° C. The mixture was then held at reflux for another 1 hour. The mixture was cooled and concentrated to yield 15.9 g of crude product. Chromatography with EtOAc/cyclohexane yielded 7.315 g (62%) of cis+trans ethyl 2-(4-chlorophenyl)-2-methyl-cyclopropanecarboxylate.

b) Preparation of cis+trans 2-(4-chlorophenyl)-2-methyl-cyclopropanecarboxylic acid A mixture of cis+trans ethyl 2-(4-chlorophenyl)-2-methyl-cyclopropanecarboxylate (6.78 g, 28.4 mmol) was added to a solution of KOH (15.9 g, 284 mmol) in methanol (300 ml). The solution was left at room temperature for 16 hours then heated at 50° C. for 4 hours and 60° C. for 2 hours. The mixture was cooled to room temperature, concentrated, shaken between dichloromethane and aqueous HCl. The aqueous was extracted twice with dichloromethane and the combined organic phases were evaporated to yield 4.718 g (79%) of a mixture of cis+trans 2-(4-chlorophenyl)-2-methyl-cyclopropanecarboxylic acid as a thick yellow oil.

1H-NMR ($CDCl_3$) 1.25 (m); 1.46 (m); 1.55 (m); 1.75 (m); 7.23 (m).

c) Preparation of racemic tert-butyl N-[(1R,2R)-2-(4-chlorophenyl)-2-methyl-cyclopropyl]carbamate A solution of a mixture of cis+trans 2-(4-chlorophenyl)-2-methyl-cyclopropanecarboxylic acid (4.508 g, 21.4 mmol), triethylamine (2.6 g, 3.6 ml, 25.7 mmol), (PhO)₂PON3 (6.48 g, 5.07 ml, 23.5 mmol) and tBuOH (20.4 ml) was heated to reflux for 18 hours. (tBuOCO)2O (7.052 g, 32.3 mmol) was added and reflux was continued for a further 2 hours. On cooling the mixture was diluted with EtOAc, washed with 5% citric acid and NaHCO₃ (1 M), dried with MgSO4 and the solvent evaporated to yield 12.1 g, which was chromatographed with EtOAc/cyclohexane to yield 1.705 g of the product mixed with its trans isomer. The mixture was separated on RP-HPLC to yield 776 mg (13%) of racemic tert-butyl N-[(1R,2R)-2-(4-chlorophenyl)-2-methyl-cyclopropyl]carbamate. M.p. 120-121° C.

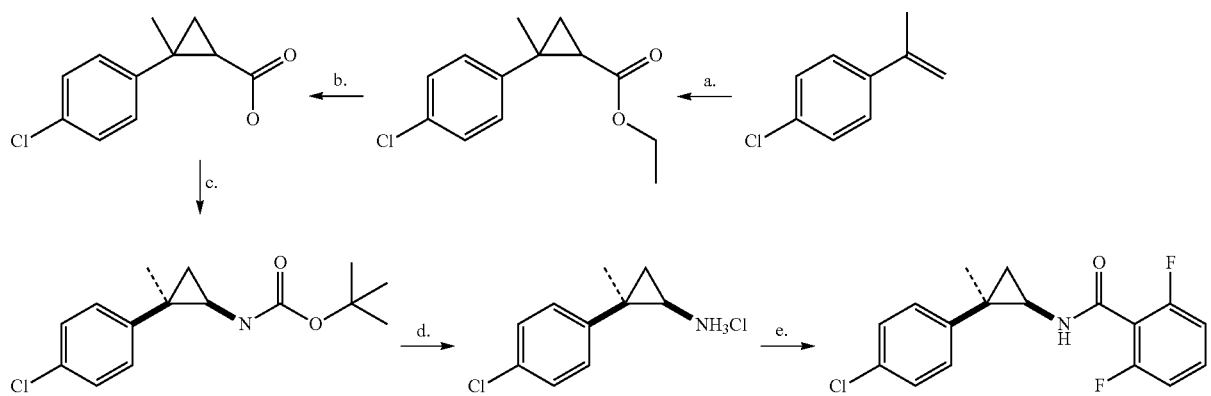

1H-NMR (CDCl3) 0.95 (1H, m); 1.07 (1H, m); 1.34 (12H, s); 2.76 (1H, m); 4.18 (1H, br s, NH); 7.27 (4H, s).

d) Preparation of racemic (1R,2R)-2-(4-chlorophenyl)-2-methyl-cyclopropanamine hydrochloride HCl (4M in dioxan, 3.24 ml, 13 mmol) was added to a solution of racemic tert-butyl N-[(1R,2R)-2-(4-chlorophenyl)-2-methyl-cyclopropyl]carbamate (731 mg, 2.60 mmol) in dichloromethane (14 ml). After 16 hours at room temperature the solvent was evaporated and the light yellow solid was stirred with tBuOMe and filtered to give racemic (1R,2R)-2-(4-chlorophenyl)-2-methyl-cyclopropanamine hydrochloride (401 mg, 71%) as a white solid.

1H-NMR (D6-DMSO) 1.12 (1H, m); 1.22 (1H, m); 1.29 (3H, s); 2.67 (1H, m); 7.46 (4H, m); 8.20 (3H, br s).

e) Preparation of racemic N-[(1R,2R)-2-(4-chlorophenyl)-2-methyl-cyclopropyl]-2,6-difluoro-benzamide 2,6-difluorobenzoyl chloride (156 mg, 0.881 mmol) was added to a rapidly stirred mixture of NaHCO3 (1 M aq., 4 ml) and a solution of racemic (1R,2R)-2-(4-chlorophenyl)-2-methyl-cyclopropanamine hydrochloride (172 mg, 0.735 mmol) in dichloromethane (4.5 ml). After stirring for 30 minutes EtOAc was added, the organic phase was separated, washed with brine, dried over MgSO4, and the solvent evaporated to give 241 mg, 100%) of racemic N-[(1R,2R)-2-(4-chlorophenyl)-2-methyl-cyclopropyl]-2,6-difluoro-benzamide. M.p. 140-142° C.

1H-NMR (CDCl$_3$) 1.11 (1H, m); 1.23 (1H, m); 1.43 (3H, s); 3.23 (1H, m); 5.50 (1H, br s, NH); 6.85 (2H, t); 7.30 (5H, m),

Example P6

Preparation of racemic N-[(1R,2R)-2-(4-chlorophenyl)-1-methyl-cyclopropyl]-2-(trifluoromethyl)benzamide (68.010)

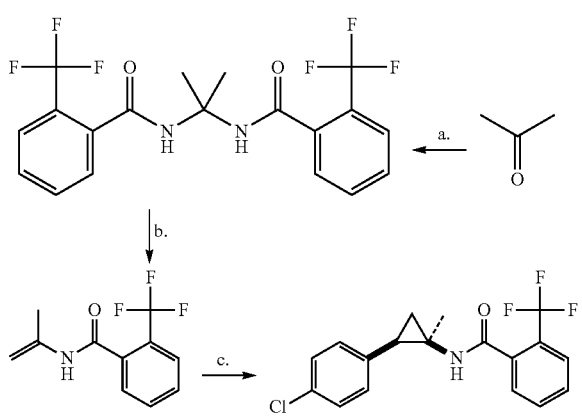

a) Preparation of N-[1-methyl-1-[[2-(trifluoromethyl)benzoyl]amino]ethyl]-2-(trifluoromethyl)benzamide Ammonia (7M in MeOH, 39.9 ml, 258 mmol) and Ti(O-iPr)$_4$ (108 ml, 101 g, 344 mmol) were added sequentially to a solution of acetone (10 g, 172 mmol) in toluene (40 ml) at 0° C. The mixture was stirred at room temperature for 18 hours, then cooled to 0° C. and triethylamine (97 ml, 70.4 g, 689 mmol) and 2-(trifluoromethyl)benzoyl chloride (51.23 ml, 72.5 g, 344 mmol) were added sequentially. A thick suspension formed. Toluene was added to aid stirring. After stirring for 2 hours at room temperature N,N,N',N'-tetrakis(2-hydroxyethyl)ethylene diamine (75.6 ml, 85.4 g, 361 mmol) in a small amount of toluene was added. The mixture was stirred at 60° C. for 15 minutes, cooled to room temperature and shaken with EtOAc and 10% aq. NH3. The organic phase was washed with water and brine, dried with Na2SO4 and evaporated to yield 46 g of a crude partially solid mixture. This was stirred with diethyl ether and the solid filtered to yield 5.5 g of crude product as a mixture with 2-(trifluoromethyl)benzamide. This was chromatographed with EtOAc/cyclohexane to yield 2.3 g (3%) of N-[1-methyl-1-[[2-(trifluoromethyl)benzoyl]amino]ethyl]-2-(trifluoromethyl)benzamide as white crystals.

1H-NMR (CDCl$_3$) 1.90 (6H, s); 6.59 (2H, br s, NH); 7.55 (6H, m); 7.70 (2H, d).

b) Preparation of N-isopropenyl-2-(trifluoromethyl)benzamide

A solution of KOtBu in THF (1 M, 4.4 ml, 4.39 mmol) was added to a solution of N-[1-methyl-1-[[2-(trifluoromethyl)benzoyl]amino]ethyl]-2-(trifluoromethyl)benzamide (1.53 g, 3.66 mmol) in THF (10 ml). After 16 hours at room temperature the mixture was cooled to 0° C. and acetic acid (0.5 ml) added, and the mixture shaken between EtOAc and water, washed with NaHCO3 (1 M), brine, dried with MgSO$_4$ and evaporated to yield 1.48 g of crude product which contained ca 20% starting material. Chromatography with EtOAc/cyclohexane yielded 451 mg (54%) N-isopropenyl-2-(trifluoromethyl)benzamide. M.p. 95-98° C.

1H-NMR (CDCl3) 1.99 (3H, s); 4.61 (1H, d); 5.53 (1H, d); 6.72 (1H, br s, NH); 7.60 (3H, m), 7.72 (1H, d).

c) Preparation of racemic N-[(1R,2R)-2-(4-chlorophenyl)-1-methyl-cyclopropyl]-2-(trifluoromethyl)benzamide 4-Fluorophenyl benzaldehyde-tosylhydrazone sodium salt from example P2b (274 mg, 0.872 mmol), N-isopropenyl-2-(trifluoromethyl)benzamide (200 mg, 872 mmol), benzyltriethylammonium chloride (20 mg, 0.087 mmol), and rhodium acetate dimer (3.9 mg, 0.0087 mmol) were stirred with dioxane (4 ml) at 75° C. for 16 hours. The mixture was shaken between Et2O and water. The organic phase was dried with MgSO$_4$ and evaporated to yield 250 mg of a crude mixture. This was chromatographed on silica with EtOAc/cyclohexane to yield 160 mg of a mixture of cis/trans isomers, which was separated further by RP-HPLC to yield 33 mg (12%) of racemic N-[1R,2R)-2-(4-chlorophenyl)-1-methyl-cyclopropyl]-2-(trifluoromethyl)benzamide. M.p. 122-125° C.

1H-NMR (CDCl$_3$) 1.34 (1H, m); 1.42 (1H, m); 1.63 (3H, s); 2.19 (1H, m); 5.48 (1H, br s, NH); 6.99 (2H, m); 7.20 (2H, m); 7.45 (3H, m); 7.59 (1H, m).

Example P7

Preparation of racemic N-[(1R,2R,3S)-2-(4-chlorophenyl)-3-methyl-cyclopropyl]-2-(trifluoromethyl)benzamide (68.008)

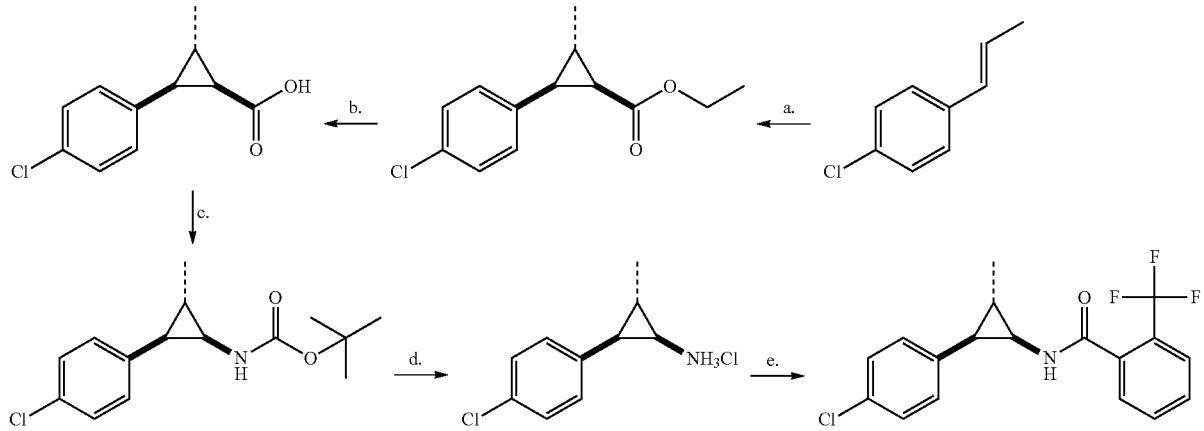

a) Preparation of racemic ethyl (1R,2S,3S)-2-(4-chlorophenyl)-3-methyl-cyclopropanecarboxylate Ethyl diazoacetate (1.61 g, 12 mmol) was added over 90 minutes to a mixture of rhodium acetate (44 mg) in E-1-(4-chlorophenyl)-1-propene (2.243 g, 12 mmol) at 90° C. with stirring. Heating was continued for 60 minutes. On cooling the mixture was chromatographed with EtoAc/hexane to yield 170 mg of racemic ethyl (1R,2S,3S)-2-(4-chlorophenyl)-3-methyl-cyclopropanecarboxylate. (Another isomer was also isolated.)

1H-NMR (CDCl3) 1.04 (3H, t); 1.26 (3H, d); 1.82 (1H, m); 2.03 (1H, m); 2.29 (1H, m); 3.92 (2H, q); 7.10-7.20 (4H, m)

b) Preparation of racemic (1R,2S,3S)-2-(4-chlorophenyl)-3-methyl-cyclopropanecarboxylic acid A solution of racemic ethyl (1R,2S,3S)-2-(4-chlorophenyl)-3-methyl-cyclopropanecarboxylate (818 mg, 3.36 mmol) and KOH (1.92 g) in methanol was heated at 80° C. for 2 hours, cooled to RT, and the solvent evaporated. The mixture was shaken between dichloromethane and water, then the aqueous phase was acidified and extracted with dichloromethane, to give the pure racemic (1R,2S,3S)-2-(4-chlorophenyl)-3-methyl-cyclopropanecarboxylic acid.

1H-NMR (CDCl3) 1.26 (3H, d); 1.80 (1H, m); 2.00 (1H, m); 2.36 (1H, m); 7.08-7.30 (4H, m)

c) Preparation of racemic tert-butyl N-[(1R,2R,3S)-2-(4-chlorophenyl)-3-methyl-cyclopropyl]carbamate A solution of racemic (1R,2S,3S)-2-(4-chlorophenyl)-3-methyl-cyclopropanecarboxylic acid (101 mg, 0.48 mmol), triethylamine (58.2 mg, 0.48 mmol), diphenyl phosphoryl azide (149.8 mg, 0.48 mmol), and tBuOH (357.6 mg) in cyclohexane (3 ml) was refluxed for 18 hours. After cooling (tBuOCO)2O (161.42 mg) was added and refluxed for a further 2 hours. After cooling to RT, the mixture was shaken between EtOAc and citric acid (5%), washed with 1M NaHCO3, dried with Na2SO4 and evaporated to give 386 mg of crude product. Chromatography with ether/hexane gave 41 mg of pure racemic tert-butyl N-[(1R,2R,3S)-2-(4-chlorophenyl)-3-methyl-cyclopropyl]carbamate.

1H-NMR (CDCl$_3$) 0.88 (1H, m); 1.23 (peak); 1.35 (peak); 1.90 (1H, m); 2.61 (1H, m); 4.25 (1H, m); 7.06 (2H, d); 7.23 (2H, d).

d) Preparation of racemic (1R,2R,3S)-2-(4-chlorophenyl)-3-methyl-cyclopropanamine hydrochloride A solution of HCl in dioxane (0.6 ml) was added to a solution of racemic tert-butyl N-[(1R,2R,3S)-2-(4-chlorophenyl)-3-methyl-cyclopropyl]carbamate. (84.5 mg) in dichloromethane (1.2 ml). The solution was left for 3 hours during which time a white precipitate had formed. The solvent was evaporated and the solid was stirred with diethyl ether, filtered off, and washed with more ether to yield 43.4 mg (83%) of racemic (1R,2R,3S)-2-(4-chlorophenyl)-3-methyl-cyclopropanamine hydrochloride 1H-NMR (CDCl3) 1.27 (3H, d); 1.57 (1H, m); 2.06 (1H, m); 2.33 (1H, m); 7.24 (4H, m); 7.95 (3H, br s, NH3).

e) Preparation of racemic N-[(1R,2R,3S)-2-(4-chlorophenyl)-3-methyl-cyclopropyl]-2-(trifluoromethyl)benzamide 2-Trifluoromethyl-benzoyl chloride (0.028 ml, 39.4 mg, 0.17 mmol) was added to a solution of racemic (1R,2R,3S)-2-(4-chlorophenyl)-3-methyl-cyclopropanamine hydrochloride (37.2 mg, 0.17 mmol), and triethylamine (43.4 mg) in THF at 0° C. with stirring, and stirred for 18 hours. The white solid of Et3NHCl was filtered off and the filtrate concentrated and chromatographed with diethyl ether/hexane to yield 20 mg of pure racemic N-[(1R,2R,3S)-2-(4-chlorophenyl)-3-methyl-cyclopropyl]-2-(trifluoromethyl)benzamide. M.p. 167-9

1H-NMR (CDCl3) 1.35 (3H, d); 1.48 (1H, m); 2.14 (1H, m); 3.01 (1H, m); 5.38 (1H, br s, NH); 7.10 (1H, m); 7.15 (2H, d); 7.28 (2H, d); 7.47 (2H, m); 7.63 (1H, m).

Tables 67, 68 and 69: Characterising Data

Tables 67, 68 and 69 show selected melting point, selected HPLC-MS, and selected NMR data for compounds of the present invention. CDCl$_3$ was used as the solvent for NMR measurements, unless otherwise stated. No attempt is made to list all characterising data in all cases.

In Tables 67, 68 and 69 and throughout the description that follows, temperatures are given in degrees Celsius; "NMR"

means nuclear magnetic resonance spectrum; HPLC is high pressure liquid chromatography; MS stands for mass spectrum; "%" is percent by weight, unless corresponding concentrations are indicated in other units. The following abbreviations are used throughout this description:

| m.p. = melting point | b.p. = boiling point. |
|---|---|
| S = singlet | br = broad |
| d = doublet | dd = doublet of doublets |
| t = triplet | q = quartet |
| m = multiplet | ppm = parts per million |

Table 67 below is a list of characterised compounds of the formula Ic. This represents formula I, wherein R2, R3, R4, and R5 are H.

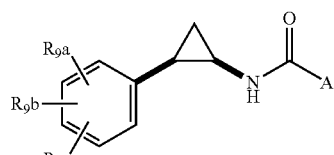

| Cpd No | R9a, R9b, R9c* | A | m.p. (° C.) |
|---|---|---|---|
| 67-001 | 4-Cl | 3-(difluoromethyl)-1-methyl-pyrazol-4-yl | 126-127 |
| 67-002 | 4-F | 3-(difluoromethyl)-1-methyl-pyrazol-4-yl | 141-143 |
| 67-003 | 4-F | 2-trifluoromethyl-phenyl | 139-140 |
| 67-004 | 2-Cl | 2-trifluoromethyl-phenyl | 118-119 |
| 67-005 | 4-Cl | 2-trifluoromethyl-phenyl | 169-170 |
| 67-006 | 4-Cl | 2,6-difluorophenyl | 198-199 |
| 67-007 | 2-F | 2,6-difluorophenyl | 150-155 |
| 67-008 | 2-Cl | 2,6-difluorophenyl | 162-163 |
| 67-009 | 4-BnO | 2,6-difluorophenyl | 149-151 |
| 67-010 | 4-BnO | 2-trifluoromethyl-phenyl | 152-154 |
| 67-011 | 4-OCHF2 | 2-trifluoromethyl-phenyl | 133-136 |
| 67-012 | 4-OCHF2 | 2,6-difluorophenyl | 136-138 |
| 67-013 | 2-Cl, 4-Br | 2,6-difluorophenyl | 182-185 |
| 67-014 | 2-Cl, 4-Cl | 2-trifluoromethyl-phenyl | 156-157 |
| 67-015 | 2-Cl, 4-Br | 2-trifluoromethyl-phenyl | 156-159 |
| 67-016 | 2,4-Cl2 | 2,6-difluorophenyl | 179-182 |
| 67-017 | 4-F | 2-tolyl | 108-111 |
| 67-108 | 4-F | 2-pyrimidinyl | 102-104 |
| 67-109 | 4-F | 3-methyl-2-pyridyl | 99-102 |
| 67-020 | 4-F | 2-trifluoromethyl-3-pyridyl | 144-146 |
| 67-021 | 2-F, 4-Cl | 2,6-difluorophenyl | 196-199 |
| 67-022 | 4-CF3 | 2,6-difluorophenyl | 180-181 |
| 67-023 | 3-F, 4-Cl | 2,6-difluorophenyl | 192-193 |
| 67-024 | 2-F, 4-Cl | 2-trifluoromethyl-phenyl | 159-161 |
| 67-025 | 3-F, 4-Cl | 2-trifluoromethyl-phenyl | 178-180 |
| 67-026 | 4-CF3 | 2-trifluoromethyl-phenyl | 174-176 |
| 67-027 | 4-F | 3-(trifluoromethyl)-1-methyl-pyrazol-4-yl | |
| 67-028 | 2-Cl, 4-Cl | 3-(trifluoromethyl)-1-methyl-pyrazol-4-yl | |
| 67-029 | 2-Cl, 4-Cl | 3-(difluoromethyl)-1-methyl-pyrazol-4-yl | |
| 67-030 | 4-F3CO | 2-trifluoromethyl-phenyl | 164-165 |
| 67-031 | 4-F3CO | 2,6-difluoro-phenyl | 165-166 |
| 67-032 | 4-Br | 2-trifluoromethyl-phenyl | 167-169 |
| 67-033 | 4-F | 2-fluorophenyl | 112-113 |
| 67-034 | 4-F | 2-chlorophenyl | 137-139 |
| 67-035 | 4-F | 2-bromophenyl | 140-141 |
| 67-036 | 4-F | 2-iodophenyl | 136-138 |
| 67-037 | 4-F | 2,6-dichlorophenyl | 148-150 |
| 67-038 | 4-F | 2-chloro-6-fluoro-phenyl | 132-134 |
| 67-039 | 4-F | 2,4,6-trifluorophenyl | 155-156 |
| 67-040 | 4-F | 2-trifluoromethyl-6-fluoro-phenyl | 142-144 |
| 67-041 | 4-F | 2-trifluoromethoxy-phenyl | 126-128 |
| 67-042 | 4-F | 2-chloro-3-pyridyl | 109-112 |
| 67-043 | 4-OCHF2 | 2-fluorophenyl | 107-108 |
| 67-044 | 4-OCHF2 | 2-chlorophenyl | 136-139 |
| 67-045 | 4-OCHF2 | 2-bromophenyl | 144-146 |
| 67-046 | 4-OCHF2 | 2-iodophenyl | 143-145 |
| 67-047 | 4-OCHF2 | 2,6-dichlorophenyl | 135-137 |
| 67-048 | 4-OCHF2 | 2-chloro-6-fluoro-phenyl | 126-129 |
| 67-049 | 4-OCHF2 | 2,4,6-trifluorophenyl | 119-121 |
| 67-050 | 4-OCHF2 | 2-trifluoromethyl-6-fluoro-phenyl | 139-141 |
| 67-051 | 4-OCHF2 | 2-trifluoromethoxy-phenyl | 95-97 |
| 67-052 | 4-OCHF2 | 2-chloro-3-pyridyl | 154-157 |
| 67-053 | 4-CN | 2-trifluoromethyl-phenyl | 185-186 |
| 67-054 | 2-CF3, 4-F | 2,6-difluoro-phenyl | 68-71 |
| 67-055 | 2-CF3, 4-F | 2-trifluoromethyl-phenyl | 109-111 |
| 67-056 | 2-Br, 4-F | 2,6-difluoro-phenyl | 115-117 |
| 67-057 | 2-Br, 4-F | 2-trifluoromethyl-phenyl | 124-127 |
| 67-058 | 4-SMe | 2-trifluoromethyl-phenyl | 156-159 |
| 67-059 | 4-cPr | 2-trifluoromethyl-phenyl | 121-124 |
| 67-060 | 4-S(O)Me | 2-trifluoromethyl-phenyl | 154-158 |
| 67-061 | 4-S(O)2Me | 2-trifluoromethyl-phenyl | 178-180 |
| 67-062 | 2-F, 4-F | 2,6-difluoro-phenyl | 142-144 |
| 67-063 | 2-F, 4-F | 2-trifluoromethyl-phenyl | 138-141 |
| 67-064 | 2-Cl, 4-F | 2,6-difluoro-phenyl | 135-140 |
| 67-065 | 2-Cl, 4-F | 2-trifluoromethyl-phenyl | 141-143 |
| 67-066 | 4-(imidazol-1yl) | 2-trifluoromethyl-phenyl | 219-220 |
| 67-067 | 2-F, 4-F, 6-F | 2,6-difluoro-phenyl | 124-127 |
| 67-068 | 2-F, 4-F, 6-F | 2-trifluoromethyl-phenyl | 111-115 |
| 67-069 | 4-OCHF2 | 2-fluoro-6-methyl-phenyl | 145-147 |
| 67-070 | 4-OCHF2 | 2-fluoro-6-methoxy-phenyl | 110-111 |
| 67-071 | 4-OCHF2 | 2-methyl-3-pyridyl | 165-167 |
| 67-072 | 4-OCHF2 | 3-methyl-2-pyridyl | 111-113 |
| 67-073 | 4-OCHF2 | 3-trifluoromethyl-2-pyridyl | 135-137 |
| 67-074 | 4-OCHF2 | 2-trifluoromethyl-3-pyridyl | 148-151 |
| 67-075 | 4-OCHF2 | 3-fluoro-2-pyridyl | 80-82 |
| 67-076 | 4-OCHF2 | 3-methyl-4-pyridazinyl | 162-165 |
| 67-077 | 4-OCHF2 | 2-chloro-3-pyrazinyl | 117-119 |

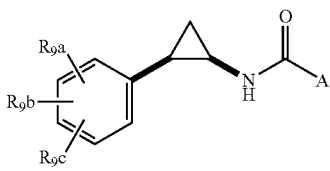

Ic

| Cpd No | $R_{9a}$, $R_{9b}$, $R_{9c}$* | A | m.p. (°C.) |
|---|---|---|---|
| 67-078 | 4-OCHF2 | 2-pyrimidinyl | — |
| 67-079 | 4-OCHF2 | 4-methyl-5-pyrimidinyl | 136-139 |
| 67-080 | 4-OCHF2 | 5-methyl-4-pyrimidinyl | 124-126 |
| 67-081 | 4-OCHF2 | 2-methyl-3-furyl | 115-116 |
| 67-082 | 4-F | 5-chloro-4-pyrimidinyl | 143-144 |
| 67-083 | 4-F | 2-methyl-3-furyl | 112-115 |
| 67-084 | 4-F | 2-methyl-3-pyridyl | 146-151 |
| 67-085 | 4-F | 3-trifluoromethyl-2-pyridyl | 138-140 |
| 67-086 | 4-F | 3-fluoro-2-pyridyl | 114-116 |
| 67-087 | 4-F | 2-chloro-3-pyrazinyl | 119-123 |
| 67-088 | 4-F | 4-methyl-5-pyrimidinyl | 162-164 |
| 67-089 | 4-F | 2-fluoro-6-methyl-phenyl | 147-150 |
| 67-090 | 4-F | 2-fluoro-6-methoxy-phenyl | 121-123 |
| 67-091 | 4-SCF3 | 2-trifluoromethyl-phenyl | 182-183 |
| 67-092 | 4-S(O)2CF3 | 2-trifluoromethyl-phenyl | 195-198 |
| 67-093 | 4-(pyrazol-1-yl) | 2-trifluoromethyl-phenyl | 218-219 |
| 67-094 | 4-S(O)CF3 | 2-trifluoromethyl-phenyl | 160-163 |
| 67-095 | 4-OCHF2 | 2-trifluoromethyl-phenyl | 134-135$^a$ |
| 67-096 | 4-OCHF2 | 2-trifluoromethyl-phenyl | 134-135$^b$ |
| 67-097 | 2,4,6-F3 | 3-trifluoromethyl-2-pyridyl | 115-118 |
| 67-098 | 2,4,6-F3 | 2-trifluoromethyl-3-pyridyl | 164-167 |

*either one or two of $R_{9a}$, $R_{9b}$, and $R_{9c}$ is hydrogen depending on the substituents defined in each row of Table 61
a: enantiomer A; b: enantiomer B Enantiomer A correspond to one of compound of formula Iaa or Iab, and enantiomer B corresponds to the remaining compound (either formula Iaa or Iab).

Table 68 below is a list of characterised compounds of the formula Id, all of which are racemic. The designation R & S in the table refers to relative stereochemistry.

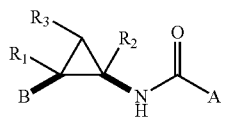

(Id)

| Cpd No | B | A | R1 | R2 | R3 | m.p. (°C.) |
|---|---|---|---|---|---|---|
| 68-001 | 4-chloro-phenyl | 2-trifluoromethyl-phenyl | 1R,2S | F | H | H | 204-206 |
| 68-002 | 4-chloro-phenyl | 3-(difluoromethyl)-1-methyl-pyrazol-4-yl | 1R,2S | F | H | H | |
| 68-003 | 4-fluoro-phenyl | 2,6-difluoro-phenyl | 1R,2R,3R | H | H | Me | 90-96 |
| 68-004 | 4-chloro-phenyl | 2-trifluoromethyl-phenyl | 1R,2R | Me | H | H | 167-168 |
| 68-005 | 2,fluoro-5-chloro-3-pyridyl | 2-iodophenyl | 1R,2R | H | H | H | 185-187 |
| 68-006 | 2,fluoro-5-chloro-3-pyridyl | 2-trifluoromethyl-phenyl | 1R,2R | H | H | H | 166-169 |
| 68-007 | 4-chloro-phenyl | 2,6-difluoro-phenyl | 1R,2R,3S | H | H | Me | 158-159 |
| 68-008 | 4-chloro-phenyl | 2-trifluoromethyl-phenyl | 1R,2R,3S | H | H | Me | 167-169 |
| 68-009 | 4-chloro-phenyl | 2,6-difluoro-phenyl | 1R,2R | Me | H | H | 140-142 |
| 68-010 | 4-fluoro-phenyl | 2-trifluoromethyl-phenyl | 1R,2R | H | Me | H | 122-125 |

Table 69 below is a list of characterised compounds of the formula Ie

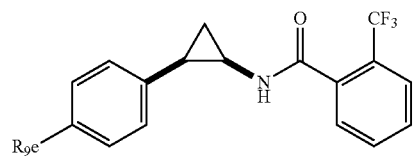

Ie

| Cpd No | R9e | retention time | M (calculated) | (M + H)+ (measured) |
|---|---|---|---|---|
| 69-001 | 3-furyl | 1.55 | 371.4 | 372.4 |
| 69-002 | 3-pyrazolyl | 1.19 | 371.4 | 372.34 |
| 69-003 | 3-pyridyl | 0.97 | 382.4 | 383.4 |
| 69-004 | 4-pyridyl | 0.85 | 382.4 | 383.4 |
| 69-005 | 5-pyrimidinyl | 1.18 | 383.4 | 383.7 |
| 69-006 | 5-methyl-2-furyl | 1.56 | 385.4 | 386.31 |
| 69-007 | 3-thienyl | 1.65 | 387.4 | 388.3 |
| 69-008 | 2-thienyl | 1.67 | 387.4 | 388.3 |
| 69-009 | 5-formyl-2-furyl | 1.37 | 399.4 | 399.7 |
| 69-010 | 2-formyl-2-furyl | 1.42 | 399.4 | 400.4 |
| 69-011 | 3-fluoro-4-pyridyl | 1.36 | 400.4 | 401.4 |
| 69-012 | 2-fluoro-4-pyridyl | 1.46 | 400.4 | 401.4 |
| 69-013 | 2-fluoro-3-pyridyl | 1.44 | 400.4 | 401.4 |
| 69-014 | 2-fluoro-5-pyridyl | 1.48 | 400.4 | 401.4 |
| 69-015 | 3-methyl-4-thienyl | 1.76 | 401.4 | 402.4 |
| 69-016 | 2-methoxy-5-pyridyl | 1.55 | 412.4 | 413.4 |
| 69-017 | 2-methoxy-3-pyridyl | 1.56 | 412.4 | 413.4 |
| 69-018 | 2-methoxy-5-pyrimidinyl | 1.35 | 413.4 | 414.4 |
| 69-019 | 2,4-dihydroxy-5-pyrimidinyl | 0.96 | 415.4 | 416.4 |
| 69-020 | 2-formyl-3-thienyl | 1.49 | 415.4 | 416.3 |

-continued

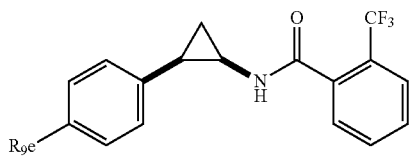

|  | R9e | retention time | M (calculated) | (M + H)+ (measured) |
|---|---|---|---|---|
| 69-021 | 2-formyl-5-thienyl | 1.49 | 415.4 | 416.3 |
| 69-022 | 2,5-dimethyl-3-thienyl | 1.88 | 415.5 | 416.4 |
| 69-023 | 6-chloro-3-pyridyl | 1.56 | 416.8 | 417.3 |
| 69-024 | 2-chloro-3-pyridyl | 1.47 | 416.8 | 417.3 |
| 69-025 | 2-chloro-4-pyridyl | 1.53 | 416.8 | 417.3 |
| 69-026 | 3-chloro-5-pyridyl | 1.55 | 416.8 | 417.3 |
| 69-027 | 5-chloro-2-pyridyl | 1.65 | 416.8 | 417.33 |
| 69-028 | 2,6-difluoro-3-pyridyl | 1.59 | 418.4 | 419.4 |
| 69-029 | 2-benzofuryl | 1.84 | 421.4 | 422.36 |
| 69-030 | 2-chloro-3-thienyl | 1.79 | 421.9 | 422.3 |
| 69-031 | 2-ethoxy-5-pyridyl | 1.67 | 426.4 | 427.2 |
| 69-032 | 2-methylthio-5-pyridyl | 1.61 | 428.5 | 492.4 |
| 69-033 | 1-acetyl-5-thienyl | 1.52 | 429.5 | 430.3 |
| 69-034 | 2-methylthio-5-pyrimidinyl | 1.54 | 429.5 | 430.4 |
| 69-035 | 2-chloro-3-methyl-5-pyridyl | 1.66 | 430.9 | 431.4 |
| 69-036 | 4-isoquinolyl | 1.2 | 432.4 | 433.4 |
| 69-037 | 2-fluoro-3-chloro-4-pyridyl | 1.62 | 434.8 | 435.3 |
| 69-038 | 2-benzothiophenyl | 1.9 | 437.5 | 438.3 |
| 69-039 | 3-benzothiophenyl | 1.88 | 437.5 | 438.3 |
| 69-040 | 2,6-dimethoxy-3-pyridyl | 1.78 | 442.4 | 443.4 |
| 69-041 | 2-methoxy-3-chloro-4-pyridyl | 1.68 | 446.9 | 447.3 |
| 69-042 | 2,2-difluoro-5-methoxy-6-pyridyl | 1.78 | 449.4 | 450.2 |
| 69-043 | 2-trifluoromethyl-5-pyridyl | 1.66 | 450.4 | 451.4 |
| 69-044 | 2-fluoro-3-quinolyl | 1.71 | 450.4 | 451.38 |
| 69-045 | 2,3-difluoro-4-pyridyl | 1.67 | 451.3 | 451.29 |
| 69-046 | 2,5-dichloro-3-pyridyl | 1.71 | 451.3 | 451.3 |
| 69-047 | 2,3-dichloro-4-pyridyl | 1.71 | 451.3 | 451.3 |
| 69-048 | 2,6-dichloro3-pyridyl | 1.71 | 451.3 | 451.3 |
| 69-049 | 3-pyrrolyl | 1.37 | 370.4 | 371.4 |
| 69-050 | 2-pyrrolyl | 1.45 | 370.4 | 371.4 |
| 69-051 | 4-pyrazolyl | 1.15 | 371.4 | 372.3 |
| 69-052 | 5-oxazolyl | 1.27 | 372.3 | 373.3 |
| 69-053 | 2,5-dichloro-3-thienyl | 2.01 | 456.3 | 456.3 |
| 69-054 | 1-methyl-4-pyrazolyl | 1.27 | 385.4 | 386.4 |
| 69-055 | 1-methyl-5-pyrazolyl | 1.29 | 385.4 | 386.4 |

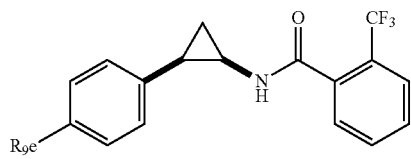

|  | R9e | retention time | M (calculated) | (M + H)+ (measured) |
|---|---|---|---|---|
| 69-056 | 1-methyl-2-pyrrolyl | 1.55 | 385.4 | 386.55 |
| 69-057 | 5-formyl-4-methyl-2-thienyl | 1.56 | 429.5 | 430.3 |
| 69-058 | 1-t-butoxy-carbonyl-2-pyrrolyl | 1.9 | 470.5 | 471.4 |
| 69-059 | 2-(4-fluorophenyl)-5-pyridyl | 1.77 | 476.5 | 477.4 |
| 69-060 | 2-methyl-4-pyridyl | 0.86 | 396.4 | 397.4 |
| 69-061 | 1,2-dimethyl-5-imidazolyl | 0.81 | 399.4 | 400.4 |
| 69-062 | 1-ethyl-4-pyrazolyl | 1.37 | 399.4 | 400.4 |
| 69-063 | 2-methyl-3-thienyl | 1.76 | 401.4 | 402.3 |
| 69-064 | 2-cyano-6-pyridyl | 1.49 | 407.4 | 408.4 |
| 69-065 | 2-cyano-5-methyl-3-furanyl | 1.65 | 410.4 | 411.4 |
| 69-066 | 1,3,5-trimethyl-4-pyrazolyl | 1.33 | 413.4 | 414.4 |
| 69-067 | 4-chloro-3-pyridyl | 1.42 | 416.8 | 417.3 |
| 69-068 | 3-Chloro-4-pyridyl | 1.46 | 416.8 | 417.3 |

The MS measurements were carried out with the ACQUITY SQD Mass Spectrometer from Waters (Single quadrupole mass spectrometer)

Ionisation method: Electrospray

Polarity: positive ions

Capillary (kV) 3.00,

Cone (V) 20.00,

Extractor (V) 3.00,

Source Temperature (° C.) 150,

Desolvation Temperature (° C.) 400,

Cone Gas Flow (L/Hr) 60,

Desolvation Gas Flow (L/Hr) 700

Mass range: 100 to 800 Da

DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Biological Examples

*Meloidogyne* spp. (Root-knot nematode) contact activity, preventive. Pouch test.

Filter papers (9 cm×4.5 cm) with a small pocket were placed into plastic pouches (12 cm×6 cm). One cucumber cv. Toshka seed was placed in the centre of the filter paper pocket of all the pouches needed for a test. The cucumber seeds in the pouches were treated with test solutions at 200 ppm by pipetting the solution directly over the cucumber seed in the filter paper pocket in the pouch. Prior to application, the compound solution was prepared at twice the concentration required and the egg suspension is prepared with FORL nutrient solution with 3000 eggs/0.5 ml. After applying all the treatments, 3000 eggs (in 0.5 ml of FORL nutrient solution) were pipetted into the pouches. The pouches were incubated in a moist chamber for twelve days and watered regularly to maintain good filter paper moisture essential for the growing cucumber root system. After this period, the filter paper containing the germinated cucumber seedling was removed from the plastic pouch to assess the number of galls caused by *Meloidogyne* spp. per root system.

The following compounds showed a greater than 80% reduction of galling compared to the untreated control: 67-055, 67-057, 67-073, 67-011, 67-063, 67-065, 67-068, 67-096, 67-067, 67-014, 67-049, 67-056, 67-042, 67-054, 67-015, 67-003, 67-064, 67-013, 67-020, 67-062, 67-036, 67-071, 67-074, 67-075, 67-077, 67-085, 67-007, 67-017, 67-034, 67-018, 67-035, 67-052, 67-086 67-021, 67-024, 67-087, 67-046 and 67-016.

*Meloidogyne* spp. (Root-knot nematode) contact activity, preventive, drench test. Cucumber cv. Toshka seeds were shown directly into pots filled with a sandy substrate. Six days later pots were each treated with 5 ml of a WP10 suspension of the test compound at 20 ppm. Hereafter pots were inoculated with 3000 eggs of *M. incognita*. The trial was harvested fourteen days after trial application and inoculation. Root galling was assessed according to Zeck's gall index (Zeck, 1971).

The following compounds showed a greater than 80% reduction of galling compared to the untreated control: 67-055, 67-057, 67-073, 67-011, 67-063, 67-065, 67-068, 67-096, 67-054, 67-003, 67-064, 67-013 67-020, 67-062, 67-071, 67-074, 67-075, 67-077, 67-085, 67-007, 67-086, 67-087, 67-084, 67-053, 67-090, 67-083, 67-089, 67-008, 67-067, 67-056, 67-017, 67-021, 67-012, 67-072, 67-014, 67-042, 67-015, 67-036, 67-034, 67-022, 67-081, 67-070, 67-088, 67-045, 67-035, 67-052, 67-024, 67-005, 67-031, 67-044, 67-016, 67-076, 67-082, 67-049, 67-043, 67-095, 67-069, 67-032, 67-026, 67-006, 67-019, 67-046 and 67-009.

Table 70 below shows the comparison of the nematicidal activity of the cis isomers, which are the subject of this present invention with their corresponding trans isomers. The trans isomers were obtained using method P3 above and separated from their cis isomers as described in method P3a. In the table below they are numbered according to their cis isomers with the suffix "trans" as shown in this example of 67-016 and 67-016 trans

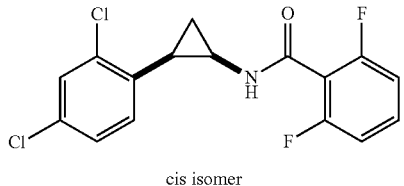

Compound 67-016 cis isomer

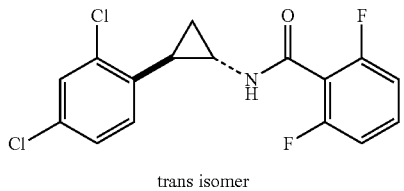

Compound 67-016 trans isomer

Biological Screen Nem 1. *Meloidogyne* spp. (Root-knot nematode) contact activity, preventive. Pouch test. Values are given in % galling.

Biological Screen Nem 2. *Meloidogyne* spp. (Root-knot nematode) contact activity, preventive, drench test. Values are given in % galling.

TABLE 70

| Cpd. No | stereochemistry | Nem 1 | Nem 2 | m.p. (° C.) |
|---|---|---|---|---|
| 67-016 | cis | 81 | 96 | 179-182 |
| 67-016trans | trans | 79 | 71 | 137-139 |
| 67-014 | cis | 100 | 98 | 156-157 |
| 67-014trans | trans | 1 | 5 | 151-153 |
| 67-026 | cis | 64 | 82 | 174-176 |
| 67-026trans | trans | 0 | 10 | 108-118 |

The invention claimed is:
1. A compound of the formula Ic

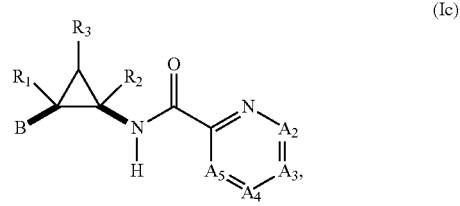

wherein
A2, A3, A4, and A5 are N, CH, or CR11, provided A3 is either CH or N and only one of A2 to A5 is N;
wherein R11 is, independently of each other, halogen, cyano, C1-C4-alkyl, C1-C4-haloalkyl, C1-C4-alkoxy, C1-C4-haloalkoxy, C1-C4-haloalkylsulfanyl, C1-C4-alkoxy-C1-C4-alkyl or C1-C4-haloalkoxy-C1-C4-) alkyl,
$R_1$, $R_2$ and $R_3$, independently of each other, are hydrogen, halogen, cyano, C1-C4-alkyl or C1-C4-haloalkyl,
B is a mono- or bicyclic 5 to 10 membered heteroaromatic ring system containing 1 to 5 heteroatoms, each independently selected from oxygen, nitrogen and sulphur, or a mono- or bicyclic 5 to 10 membered aromatic ring system, wherein the heteroaromatic ring system or the aromatic ring system is unsubstituted or substituted by R9, where R9 is, independently of each other, halogen, cyano, R8, —OR8, —C(O)R8, —OC(O)R8, —NR7R8, —NR7C(O)R8, —NR7S(O)nR8, —S(O)nR8, —S(O)nNR7R8, —C(O)OR8 or C(O)NR7R8, where n is 0, 1, or 2, R7 is, independently of each other, hydrogen, C1-C4-alkyl, C1-C4-haloalkyl, benzyl or phenyl, where benzyl or phenyl is unsubstituted or substituted with halogen, cyano, C1-C4-alkyl or C1-C4-haloalkyl, and R8 is, independently of each other, C1-C4-alkyl, which is unsubstituted or substituted by R10, C3-C6-cycloalkyl, which is unsubstituted or substituted by R10, C6-C14-bicycloalkyl, which is unsubstituted or substituted by R10, C2-C4-alkenyl, which is unsubstituted or substituted by R10, C2-C4-alkynyl, which is unsubstituted or substituted by R10, phenyl, which is unsubstituted or substituted by R10, or heteroaryl, which is unsubstituted or substituted by R10, where R10 is, independently of each other, hydroxyl, halogen, cyano, C1-C4-alkyl, C1-C4-haloalkyl, C1-C4-alkoxy, C1-C4-haloalkoxy, C1-C4-alkylthio, C1-C4-haloalkylthio, C2-C4-alkenyloxy, C2-C4-alkynyloxy, formyl, C1-C4-alkylcarbonyl, C1-C4alkoxycarbonyl or halophenyl, wherein B and A-CO—NR5 are cis to each other on the cyclopropyl ring, and tautomers, enantiomers of these compounds.

2. The compound according to claim 1 wherein R11 is, independently of each other, halogen, cyano, C1-C4-alkyl, or C1-C4-haloalkyl, $R_1$ is hydrogen, halogen or C1-C4-alkyl, $R_2$ and $R_3$ is, independently of each other, hydrogen or C1-C4-alkyl, B is a mono- 5 to 10 membered heteroaromatic ring system containing 1 nitrogen atom, or a mono- 5 to 10 membered aromatic ring system, wherein the heteroaromatic ring system or the aromatic ring system is substituted by one or more R9, where R9 is, independently of each other, halogen, cyano, R8, —OR8, —S(O)nR8, where n is 0, 1, or 2, R8 is, independently of each other, C1-C4-alkyl, which is unsubstituted or substituted by R10, C3-C6-cycloalkyl, which is unsubstituted or substituted by R10, phenyl, which is unsubstituted or substituted by R10 or heteroaryl, which is unsubstituted or substituted by R10, where R10 is halogen, cyano, or C1-C4-haloalky; provided where R8 is heteroaryl, R10 is halogen, cyano, C1-C4-alkyl, C1-C4-haloalkyl, C1-C4-alkoxy, C1-C4-haloalkoxy, C1-C4-alkylthio, C1-C4-alkylcarbonyl, or C1-C4alkoxycarbonyl, wherein B and A-CO—NR5 are cis to each other on the cyclopropyl ring.

3. The compound according to claim 2, wherein A2, A4 and A5 are independently selected from CH or CR11, wherein R11 is independently selected from halogen, cyano, C1-C4-alkyl, or C1-C4-haloalkyl, $R_1$ is hydrogen, or halogen, $R_2$ and $R_3$ is, independently of each other, hydrogen or C1-C4-alkyl, B is a pyridyl or phenyl, which are, independent of each other, is substituted by one or more R9, where R9 is, independently of each other, selected from halogen, cyano, C1-C4-alkyl, C1-C4-alkoxy, C1-C4-haloalkyl, C1-C4-haloalkoxy, C3-C6-cycloalkyl and C1-C4-haloalkyl-C3-C6-cycloalkyl, wherein B and A-CO—NR5 are cis to each other on the cyclopropyl ring.

4. A compound of the formula Vb

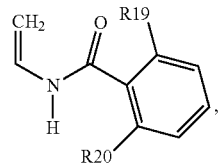

(Vb)

wherein R19 and R20, independantly of each other, are hydrogen, halogen, cyano, $C_1$-$C_3$alkyl, $C_1$-$C_3$haloalkyl, with the proviso that at least one of R19 and R20 is different from hydrogen.

5. A compound of the formula VI

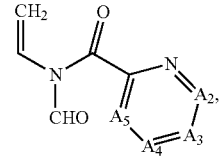

(VI)

wherein A2, A3, A4, and A5 are as defined in claim 1.

6. A pesticidal composition, which, in addition to comprising formulation adjuvants, comprises a pesticidal effective amount of a compound of the formula I according to claim 1.

7. The composition according to claim 6, which further comprises one or more other biologically active agents.

8. A method of controlling damage and/or yield loss caused by a pest and/or fungi which comprises applying to a pest, to a locus of a pest, or to a plant susceptible to attack by a pest and/or fungi or to a plant propagation material an effective amount of a compound of formula (I) as defined in claim 6.

9. A method for protecting plant propagation material from damage and/or yield loss caused by a pest and/or fungi which comprises applying to the propagation material or the site, where the propagation material is planted, an effective amount of a compound of formula (I) as defined in claim 6.

10. The method according to claim 8 wherein the damage or loss is caused by a nematode pest.

11. A treated plant propagation material, wherein adhered to the plant propagation material is an effective amount of a compound of formula (Ic) as defined in claim 1.

12. A pharmaceutical composition for the control of helminths, arachnids or arthropodal endo- or ectoparasites which comprises a compound of formula (Ic) as defined in claim 1, a physiologically tolerable carrier and optionally one or more customary formulation auxiliaries.

13. A pharmaceutical composition comprising a compound defined in claim 1, a physiologically tolerable carrier, and optionally one or more customary formulation auxiliaries for preventing infection with diseases transmitted through helminths, arachnids or arthropodal endo- or ectoparasites.

14. The composition according to claim 12 further comprising one or more other biologically active compounds.

15. A method of controlling and preventing endo- and ectoparasitic nematode infestations and infections in warm-blooded animals, which comprises injecting, topically applying or orally administering a composition according to claim 12.

* * * * *